United States Patent
Sholev et al.

(10) Patent No.: US 11,730,461 B2
(45) Date of Patent: Aug. 22, 2023

(54) STEERABLE MEDICAL DEVICE

(71) Applicant: Human Xtensions Ltd., Netanya (IL)

(72) Inventors: Mordehai Sholev, Moshav Amikam (IL); Yuval Blyakhman, Tel-Aviv (IL)

(73) Assignee: Human Xtensions Ltd., Netanya (IL)

( * ) Notice: Subject to any disclaimer, the term of this patent is extended or adjusted under 35 U.S.C. 154(b) by 598 days.

(21) Appl. No.: 16/711,628

(22) Filed: Dec. 12, 2019

(65) Prior Publication Data

US 2020/0113557 A1 Apr. 16, 2020

Related U.S. Application Data

(63) Continuation of application No. 15/120,522, filed as application No. PCT/IL2015/050342 on Mar. 31, 2015, now abandoned.

(Continued)

(51) Int. Cl.
*A61B 17/00* (2006.01)
*A61B 1/005* (2006.01)
(Continued)

(52) U.S. Cl.
CPC ...... *A61B 17/00234* (2013.01); *A61B 1/0055* (2013.01); *A61B 1/0057* (2013.01);
(Continued)

(58) Field of Classification Search
CPC ........... A61B 2017/00314; A61B 2017/00318; A61B 2017/00323; A61B 2017/00327;
(Continued)

(56) References Cited

U.S. PATENT DOCUMENTS 2,498,692 A 2/1951 Mains
4,753,223 A 6/1988 Bremer
(Continued)

FOREIGN PATENT DOCUMENTS

CN 101106945 1/2008
CN 102821669 12/2012
(Continued)

OTHER PUBLICATIONS

Requisition by the Examiner dated Feb. 11, 2022 From the Innovation, Science and Economic Development Canada, Canadian Intellectual Property Office Re. Application No. 2,938,788 witHClaims. (6 Pages).

(Continued)

*Primary Examiner* — Darwin P Erezo
*Assistant Examiner* — Erin L Colello

(57) ABSTRACT

A medical device is provided. The medical device includes an elongated device body having a steerable portion including a plurality of segments. The segments are co-axially mounted over at least one elongated elastic element which is configured for limiting rotation of the segments with respect to each other. The medical device also includes a control wire running alongside the elongated device body and being unrestrained at the steerable portion such that tensioning of the control wire angles the steerable portion from a longitudinal axis of the elongated device body and deflects the control wire away from the steerable portion.

8 Claims, 24 Drawing Sheets

Related U.S. Application Data

(60) Provisional application No. 61/972,518, filed on Mar. 31, 2014.

(51) Int. Cl.
    *A61B 17/29*     (2006.01)
    *A61M 25/01*     (2006.01)
    *A61B 1/00*     (2006.01)
    *A61B 34/30*     (2016.01)
    *G02B 23/24*     (2006.01)

(52) U.S. Cl.
    CPC .......... *A61B 17/29* (2013.01); *A61M 25/0136* (2013.01); *A61M 25/0147* (2013.01); *A61B 1/0011* (2013.01); *A61B 2017/00314* (2013.01); *A61B 2017/00323* (2013.01); *A61B 2017/00738* (2013.01); *A61B 2017/291* (2013.01); *A61B 2017/2901* (2013.01); *A61B 2017/2905* (2013.01); *A61B 2017/2908* (2013.01); *A61B 2017/2919* (2013.01); *A61B 2017/2927* (2013.01); *A61B 2034/302* (2016.02); *G02B 23/2476* (2013.01)

(58) Field of Classification Search
    CPC .. A61B 2017/00331; A61B 2017/2901; A61B 2017/2905; A61B 2017/2908; A61B 2017/2927; A61B 2017/00305; A61B 2017/003; A61B 2017/00234; A61B 17/29; A61B 1/0055; A61B 1/0056; A61B 1/0057; A61B 1/008; A61B 2034/301; A61B 2034/305; A61B 2034/306; A61B 2017/2919; A61B 17/00234; A61M 25/0105; A61M 25/0133; A61M 25/0147; A61M 2025/015; A61M 2025/0161
    See application file for complete search history.

(56) References Cited

U.S. PATENT DOCUMENTS

| | | | |
|---|---|---|---|
| 5,042,707 | A | 8/1991 | Taheri |
| 6,036,636 | A | 3/2000 | Motoki et al. |
| 7,682,307 | B2 | 3/2010 | Danitz et al. |
| 8,333,780 | B1 | 12/2012 | Pedros et al. |
| 8,419,720 | B1 | 4/2013 | Dawoodjee |
| 8,845,622 | B2 | 9/2014 | Paik et al. |
| 2003/0036748 | A1 | 2/2003 | Cooper et al. |
| 2003/0135204 | A1 | 7/2003 | Lee et al. |
| 2003/0208219 | A1 | 11/2003 | Aznoian et al. |
| 2004/0199052 | A1 | 10/2004 | Banik et al. |
| 2005/0182298 | A1 | 8/2005 | Ikeda et al. |
| 2005/0273084 | A1 | 12/2005 | Hinman et al. |
| 2005/0273085 | A1 | 12/2005 | Hinman et al. |
| 2006/0111210 | A1* | 5/2006 | Hinman .............. A61B 17/32 474/206 |
| 2007/0225681 | A1 | 9/2007 | House |
| 2008/0051802 | A1 | 2/2008 | Schostek et al. |
| 2008/0221393 | A1 | 9/2008 | Padget et al. |
| 2008/0243064 | A1 | 10/2008 | Stahler et al. |
| 2009/0182268 | A1 | 7/2009 | Thielen et al. |
| 2009/0192495 | A1 | 7/2009 | Ostrovsky et al. |
| 2009/0259141 | A1 | 10/2009 | Ewers et al. |
| 2010/0160735 | A1* | 6/2010 | Bakos .............. A61B 17/3417 600/141 |
| 2011/0118543 | A1* | 5/2011 | Dosher ................ A61B 18/22 600/114 |
| 2011/0295242 | A1 | 12/2011 | Spivey et al. |
| 2012/0022554 | A1 | 1/2012 | Paik et al. |
| 2012/0083770 | A1 | 4/2012 | Paik et al. |
| 2012/0065628 | A1 | 5/2012 | Naito |
| 2012/0197239 | A1 | 8/2012 | Smith et al. |
| 2013/0281924 | A1* | 10/2013 | Shellenberger ........ A61B 17/29 604/95.01 |
| 2014/0066924 | A1 | 3/2014 | Azamian et al. |
| 2014/0371764 | A1* | 12/2014 | Oyola .................... A61B 1/008 606/130 |
| 2016/0128767 | A1* | 5/2016 | Azamian ............ A61B 18/1492 606/41 |
| 2017/0007224 | A1 | 1/2017 | Sholev et al. |

FOREIGN PATENT DOCUMENTS

| | | | | |
|---|---|---|---|---|
| JP | 04-028335 | | 1/1992 | |
| JP | 2000-193893 | | 7/2000 | |
| JP | 2002-000622 | | 1/2002 | |
| JP | 2006-521882 | | 9/2006 | |
| JP | 2012-522553 | | 9/2012 | |
| WO | WO 2007/136829 | | 11/2007 | |
| WO | WO 2009/117696 | | 9/2009 | |
| WO | WO 2010/112608 | | 10/2010 | |
| WO | WO-2010112608 | A1 * | 10/2010 | ............. A61B 17/29 |
| WO | WO-2013039999 | A2 * | 3/2013 | ........... A61B 1/0056 |
| WO | WO 2014/125498 | | 8/2014 | |
| WO | WO 2015/151093 | | 10/2015 | |

OTHER PUBLICATIONS

Brief Communication: Oral Proceedings dated Oct. 4, 2019 From the European Patent Office Re. Application No. 15772745.4. (6 Pages).
Communication Pursuant to Article 94(3) EPC dated Jul. 18, 2018 From the European Patent Office Re. Application No. 15772745.4. (5 Pages).
Decision to Refuse A European Patent Application (Art. 97(2) EPC) dated Oct. 30, 2019 From the European Patent Office Re. Application No. 15772745.4. (4 Pages).
Examination Report dated Dec. 19, 2018 From the Australian Government, IP Australia Re. Application No. 2015242144. (5 Pages).
International Preliminary Report on Patentability dated Oct. 13, 2016 From the International Bureau of WIPO Re. Application No. PCT/IL2015/050342.
International Search Report and the Written Opinion dated Sep. 8, 2015 From the International Searching Authority Re. Application No. PCT/IL2015/050342.
Invitation to Pay Additional Fees dated Jul. 1, 2015 From the International Searching Authority Re. Application No. PCT/IL2015/050342.
Notice of Reason for Rejection dated Feb. 26, 2019 From the Japan Patent Office Re. Application No. 2016-550873. (6 Pages).
Notice of Reasons for Rejection dated Oct. 9, 2018 From the Japan Patent Office Re. Application No. 2016-550873 and Its Translation Into English. (18 Pages).
Notification of Office Action and Search Report dated Jun. 2, 2017 From the State Intellectual Property Office of the People's Republic of China Re. Application No. 201580015552.2 and Its Summary Into English. (13 Pages).
Notification of Office Action and Search Report dated Dec. 13, 2017 From the State Intellectual Property Office of the People's Republic of China Re. Application No. 201580015552.2 and Its Summary in English. (10 Pages).
Office Action dated Dec. 22, 2019 From the Israel Patent Office Re. Application No. 247578 and Its Translation Into English. (6 Pages).
Official Action dated Apr. 4, 2018 From the US Patent and Trademark Office Re. U.S. Appl. No. 15/120,522. (26 pages).
Official Action dated Sep. 29, 2019 From the US Patent and Trademark Office Re. U.S. Appl. No. 15/120,522. (34 pages).
Pre-Appeal Examination Report dated Aug. 2, 2019 From the Japan Patent Office Re. Application No. 2016-550873 and Its Translation into English. (11 Pages).
Summons to Attend Oral Proceedings Pursuant to Rule 115(1) EPC Dated Mar. 14, 2019 From the European Patent Office Re. Application No. 15772745.4. (7 Pages).
Supplementary European Search Report and the European Search Opinion dated Nov. 8, 2017 From the European Patent Office Re. Application No. 15772745.4. (9 Pages).

(56) References Cited

OTHER PUBLICATIONS

Examination Report Under Sections 12 & 13 of the Patents Act, 1970 and the Patents Rules, 2003 dated Jan. 28, 2022 From the Government of India, Intellectual Property India, Patents, Designs, Trade Marks, Geographical Indications, The Patent Office Re. Application No. 202128004075.(5 Pages).

Requisition by the Examiner dated May 14, 2021 From the Innovation, Science and Economic Development Canada, Canadian Intellectual Property Office Re. Application No. 2,938,788. (4 Pages).

European Search Report and the European Search Opinion dated Apr. 3, 2020 From the European Patent Office Re. Application No. 19204431.1. (7 Pages).

Examination Report Under Sections 12 & 13 of the Patents Act, 1970 and the Patents Rules, 2003 dated Nov. 3, 2020 From the Government of India, Intellectual Property India, Patents, Designs, Trade Marks, Geographical Indications Re. Application No. 201627030115. (5 Pages).

Office Action and Search Report dated Nov. 26, 2020 From the Israel Patent Office Re. Application No. 274090. (8 Pages).

Examination Report dated Jul. 2, 2021 From the Instituto Mexicano de la Propiedad Industrial, Direccion Divisional de Patentes Re. Application No. MX/a/2016/012110 and Its Translation Into English. (8 Pages).

Notification of Office Action and Search Report dated Dec. 13, 2017 From the State Intellectual Property Office of the People's Republic of China Re. Application No. 201580015552.2 and Its Summary in English. (15 Pages).

Final Official Action dated Nov. 23, 2022 from the US Patent and Trademark Office Re. U.S. Appl. No. 16/711,628. (18 pages).

Requisition by the Examiner dated Nov. 2, 2022 From the Innovation, Science and Economic Development Canada, Canadian Intellectual Property Office Re. Application No. 2,938,788 with Claims. (6 Pages).

Requisition by the Examiner dated Mar. 27, 2023 From the Innovation, Science and Economic Development Canada, Canadian Intellectual Property Office Re. Application No. 2,938,788. (6 Pages).

* cited by examiner

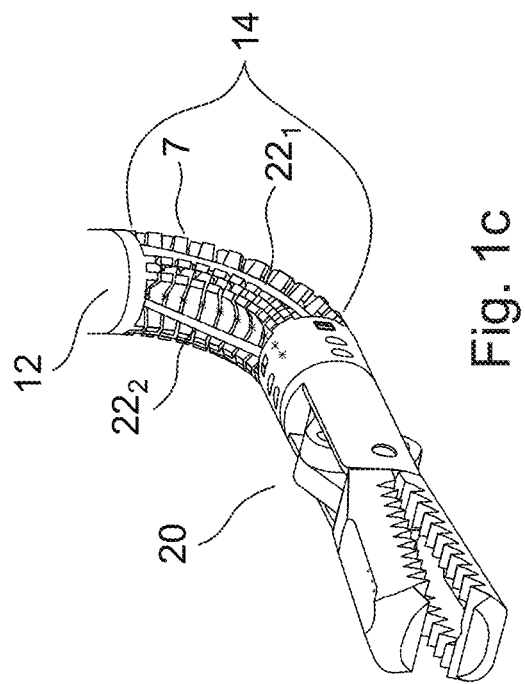
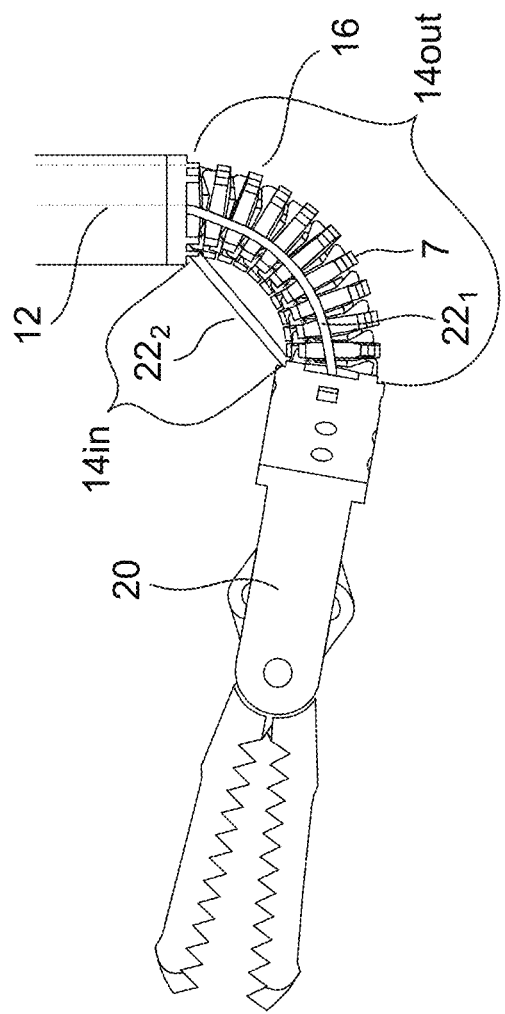
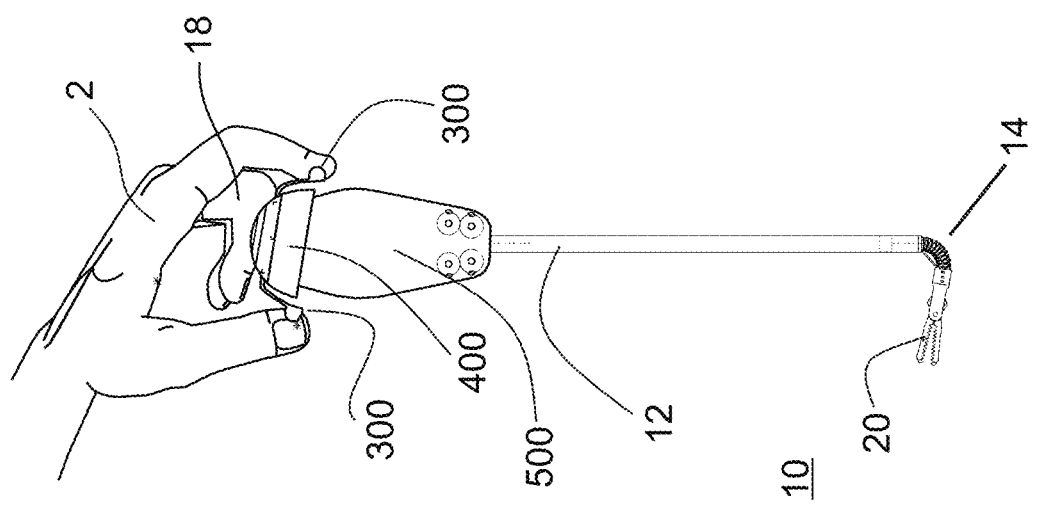

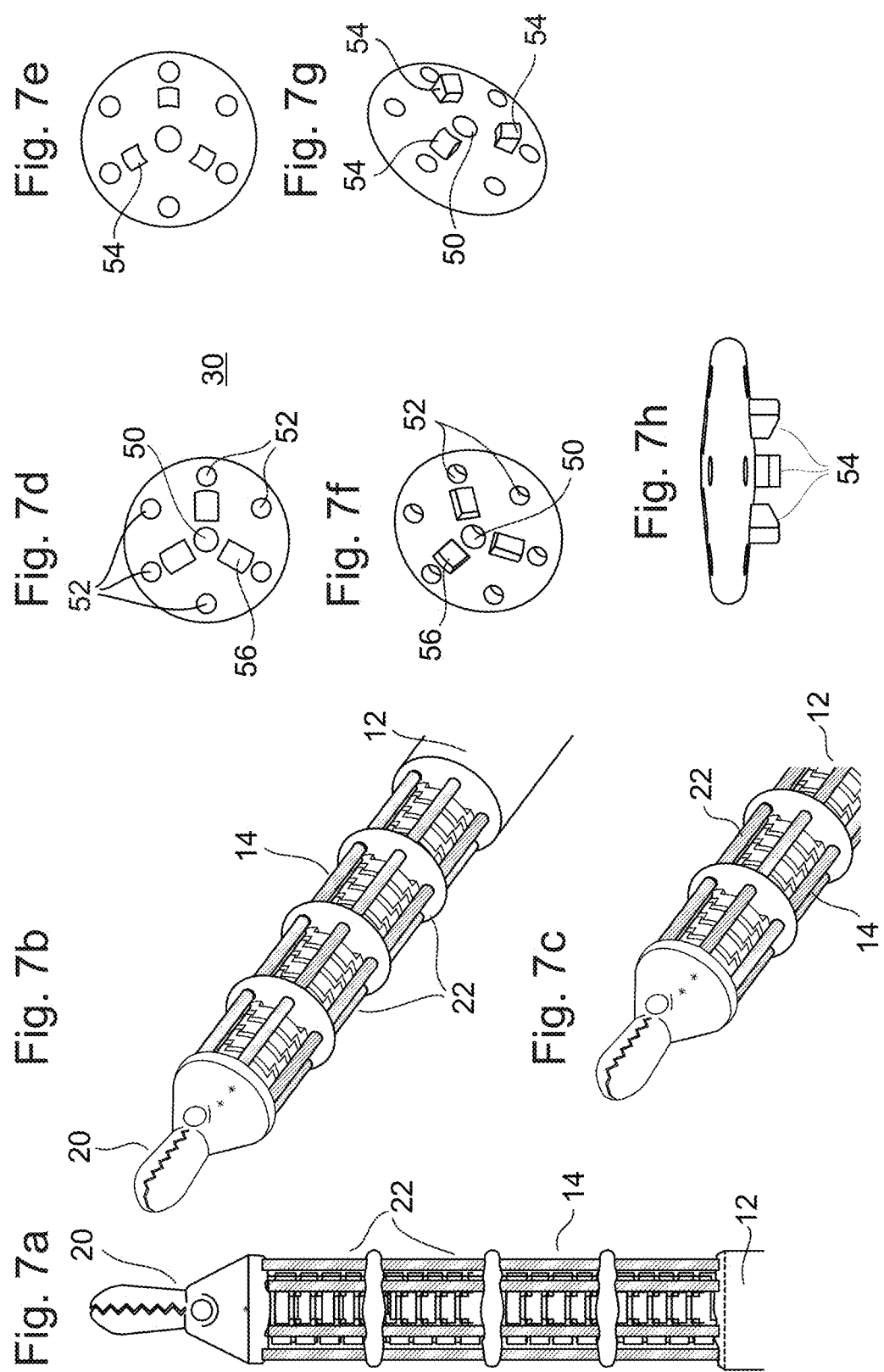

Design algorithm

Fig. 13
| | Wire travel length at 90° | Wire travel length at 45° | Holding Force at 90° (kg) | Holding Force at 45° (kg) | Articulation unit |
|---|---|---|---|---|---|
| 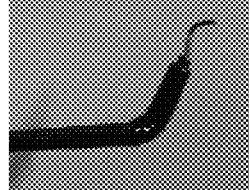 | | | 6 | 3.5 | Cambridge |
| 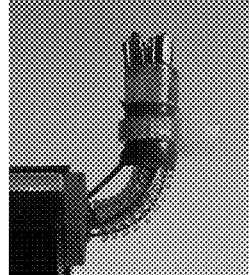 | 4 | 1.5 | 1 | 0.7 | Present device 5mm |
| 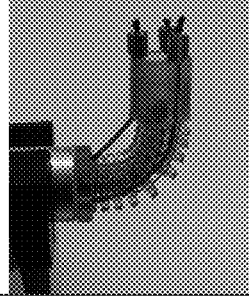 | 5 | | 0.6 | | Present device 8mm |

STEERABLE MEDICAL DEVICE

RELATED APPLICATIONS

This application is a continuation of U.S. patent application Ser. No. 15/120,522 filed on Aug. 21, 2016, which is a National Phase of PCT Patent Application No. PCT/IL2015/050342 having International Filing Date of Mar. 31, 2015, which claims the benefit of priority under 35 USC § 119(e) of U.S. Provisional Patent Application No. 61/972,518 filed on Mar. 31, 2014. The contents of the above applications are all incorporated by reference as if fully set forth herein in their entirety.

FIELD AND BACKGROUND OF THE INVENTION

The present invention relates to a steerable medical device and, more particularly, to a medical device which includes unrestrained control wires capable of deflecting away from the steerable portion of the medical device when tensioned.

Medical devices such as endoscopes and catheters are widely used in minimally invasive surgery for viewing or treating organs, cavities, passageways, and tissues. Generally, such devices include an elongated device body which is designed for delivering and positioning a distally-mounted instrument (e.g. scalpel, grasper or camera/camera lens) within a body cavity, vessel or tissue.

Since such devices are delivered though a delivery port which is positioned through a small incision made in the tissue wall (e.g. abdominal wall), and are utilized in an anatomically constrained space, it is desirable that the medical device or at least a portion thereof be steerable, or maneuverable inside the body using controls positioned outside the body (at the proximal end of the medical device). Such steering enables an operator to guide the device within the body and accurately position the distally-mounted instrument at an anatomical landmark.

In order to control deflection of a steerable portion of the device and thus steer the instrument mounted thereon, steerable medical devices typically employ one or more control wires which run the length of the device and terminate at the distal end of the steerable portion or at the distal tip.

The proximal end of each control wire is connected to the user operated handle; pulling of the wire bends the device body and deflects the steerable portion with relation the pulled wire.

Numerous examples of steerable devices are known in the art, see for example, U.S. Pat. Nos. 2,498,692; 4,753,223; 6,126,649; 5,873,842; 7,481,793; 6,817,974; 7,682,307 and U.S. Patent Application Publication No. 20090259141.

Although prior art devices can be effectively steered inside the body, the relatively small diameter of the elongated device body (which is dictated by the diameter of the delivery port), severely limits angle-of-deflection capabilities and increases the pull force required to deflect the steerable device portion.

As such, it would be highly advantageous to have a steerable medical device having a device body narrow enough for delivery through standard delivery ports and yet capable of providing wide angle steering of the deflectable portion within the body while minimizing the pull force required for such steering.

SUMMARY OF THE INVENTION

According to one aspect of the present invention there is provided medical device comprising: (a) an elongated device body having a steerable portion including a plurality of segments; (b) optionally, at least one elongated elastic element running through the plurality of segments and being configured for limiting rotation of the segments with respect to each other; and (c) at least one control wire running alongside the elongated device body and being unrestrained at the steerable portion such that tensioning of the at least one control wire angles the steerable portion from a longitudinal axis of the elongated device body and deflects the at least one control wire away from the steerable portion.

According to further features in preferred embodiments of the invention described below, each of the plurality of segments is configured so as to limit rotation thereof with respect to flanking segments.

According to still further features in the described preferred embodiments the at least one elongated elastic element has a rectangular cross section.

According to still further features in the described preferred embodiments the medical further comprises an elastic tubular sheath covering the steerable portion.

According to still further features in the described preferred embodiments the medical device comprises a plurality of control wires, each being for angling the steerable portion of the elongated device body in a specific direction.

According to still further features in the described preferred embodiments the plurality of segments are interlinked.

According to still further features in the described preferred embodiments the medical device further comprises a tissue manipulator attached to a distal end of the elongated device body.

According to still further features in the described preferred embodiments the tissue manipulator is a grasper, a tissue cutter, or a needle holder.

According to still further features in the described preferred embodiments the medical device further comprises a rigid sheath covering non-steerable portion of the elongated device body.

According to still further features in the described preferred embodiments the elongated elastic element is a spring coil.

According to still further features in the described preferred embodiments rotation between adjacent segments of the plurality of segments is limited by tab-slot engagement between the adjacent segments.

According to still further features in the described preferred embodiments the control wire is trapped between the device body and the rigid sheath at the non-steerable portion.

According to still further features in the described preferred embodiments the medical device further comprises at least one retractable lever positioned at a distal end of the steerable portion, the at least one retractable lever being attached to a distal end of the at least one control wire.

According to another aspect of the present invention there is provided a medical device comprising: (a) an elongated device body having a steerable portion including an elastic shaft; and (b) at least one control wire running alongside the elongated device body and being unrestrained at the steerable portion such that tensioning of the at least one control wire angles the steerable portion from a longitudinal axis of the elongated device body and deflects the at least one control wire away from the steerable portion.

According to still further features in the described preferred embodiments the at least one control wire is routed through a pair of guide clamps flanking the steerable portion.

The present invention successfully addresses the shortcomings of the presently known configurations by providing a steerable medical device having a deflectable region being configured capable of angling more than 180 degrees with respect to a longitudinal axis of the device.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-1h illustrate the present device and the operation of the handle controlling the deflection of the steerable portion(s) and effector end.

FIGS. 7a-7h illustrate an embodiment of the present device that includes a steerable portion fabricated from interconnected disc-shaped links. FIGS. 7a-c illustrate isometric and side views of the device, while FIGS. 7d-h illustrate the disc-shaped links.

FIG. 9b illustrates deflection of the shaft between guides.

FIG. 9i illustrates deflection of the shaft between guides.

FIG. 13 summarizes the test results of two prototypes and a prior art Cambridge articulation unit.

DESCRIPTION OF THE PREFERRED EMBODIMENTS

Figure 1F:
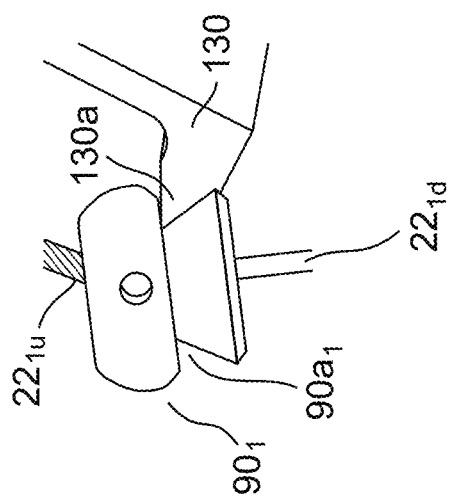

The present invention is of a medical device and system which can be used in minimally invasive surgery. Specifically, the present invention can be used to provide enhanced steering.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Steerable medical devices for use in minimally invasive surgery are well known in the art. Such devices typically utilize one or more control wires operable from a proximal end of the device positioned within the body to deflect and thus steer a distal portion of the device positioned within the body. In order to enable the control wire to efficiently deflect the distal portion of the device, the longitudinal axis of the control wire must be offset from the axis of deflection. In general, the greater the offset, the greater deflection that can be achieved with less pulling force applied to the control wire.

Since the diameter of minimally invasive devices is dictated by the delivery port used to gain access to the intrabody tissues (typically 5, 8 or 10 mm), in existing tools the offset between the control wire and the deflection axis is in fact limited by the diameter of the tool's shaft the diameter of the port and the configuration of the device.

To overcome this limitation, the present inventor has devised a unique control wire guide configuration which minimizes the overall diameter of the device body and yet provides control wire offset when the steerable portion is angled.

Thus, according to one aspect of the present invention there is provided a medical device which includes a steerable intrabody portion capable of being steered through a wide range of angles (up to 180 degrees) and patterns such as zigzag or varied diameter curves at one or more points along its length.

As used herein, the phrase "medical device" refers to any device utilizable in treatment of a subject, preferably a human subject. The medical device of the present invention is preferably used in minimally invasive surgery wherein a steerable distal portion thereof positioned within a body of a subject is controlled from a proximal end positioned outside the body (extra corporeally) via a control mechanism which preferably includes control wires. The medical device can be used for viewing or for manipulating tissues within any body cavity. Examples of medical devices which can benefit from the present invention include an endoscope (e.g. laparoscope or thorascope), a catheter, a needle holder, grasper, Scissors, hook, stapler, retractor and the like.

Figure 10A:
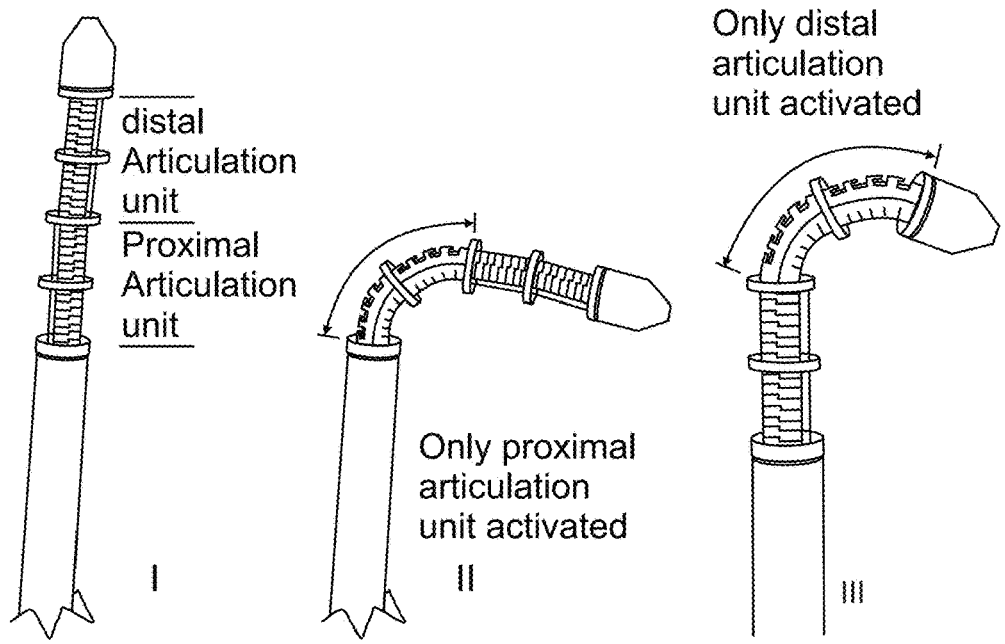
FIGS. 10a-10c are images of a prototype device tested through various articulation states and deflection angles of the steerable portion.
Figure 10B:
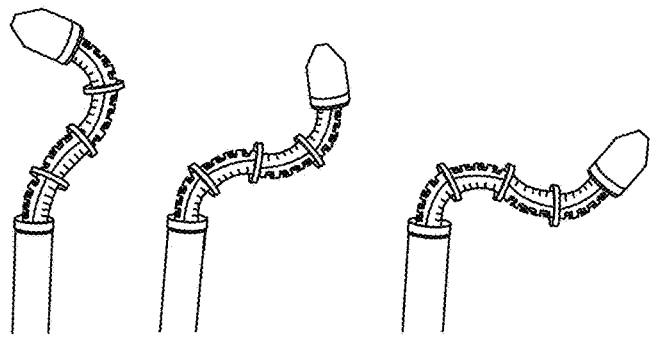
Figure 10C:
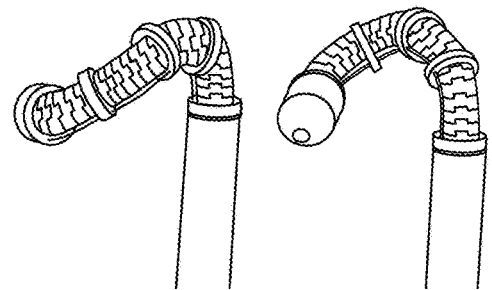

The medical device of the present invention includes an elongated device body having a distal portion which is steerable within a body of a subject (also referred to herein as steerable portion), preferably via at least one control wire. As is further described herein, the steerable portion of the device can be deflected in various directions and configurations, e.g. the entire steerable portion can be deflected (arced) towards one direction using a single control wire, or a first segment of the steerable portion can be deflected in one direction while another can be deflected in an opposite direction (zigzag and multi-plane articulation) using two or more control wires. FIGS. 10a-c of the Examples section which follows provides several examples the deflection capabilities of the present device.

The elongated device body includes one or more control wires disposed along its length. The proximal end of the control wire is attached to control levers which are actuatable by a handle of the medical device or by an electromechanical mechanism. The distal end of the control wire is attached to the device body (at a point past the steerable portion). The length of the control wire can be routed within or alongside the device body with the section of wire corresponding to the steerable portion being routed outside the device body such that it can freely move out from the longitudinal axis of the device body (offset) when the steerable portion is angled.

Enabling the control wire to freely move away from the device body at the steerable portion provides several advantages:

(i) gradually reduces the force needed to deflect the steerable portion once the steerable portion curves;

(ii) negates the need for wire guides at the steerable portion (an optionally along the entire device body) thus simplifying construction and reducing friction on the control wires;

(iii) reduce the friction between the wire and the wire guides;

(iv) allows to use smaller diameter wires because the force needed to steer the articulation is significantly smaller;

(v) reduces the means of connecting the wire to the distal end of the articulation because the force needed to steer the articulation is significantly smaller;

(vi) (iv)+(v) allows to reduce the diameter of the device when linear thus facilitating insertion and removal into body (through, for example, a trocar port);

(vii) when using the tool manually, all the above a allows the surgeon to operate the tool with much less effort;

(viii) makes the use of electro-mechanic actuators possible. As it will be described later the significant force reducing allows the use of very small actuators (such as motors) which enables the design of a light weight fully motorized device;

(ix) The use of very small actuators (such as motors) enables to operate a fully motorized device with small energy consumption; and (X) Enabling use of transparent materials in the steerable portion.

FIGS. 1a-11b illustrate several embodiments of the present device which is referred to herein as device 10.

FIG. 1a illustrates a laparoscopic configuration of device 10. Device 10 includes an elongated device body 12 (also referred to herein as elongated body 12 or body 12) which includes a steerable portion 14 fabricated from a series of segments 30 (shown in FIGS. 5a-5c).

Device body 12 can be 20-40 cm in length and 5-12 mm in diameter. Device body 12 can be hollow or solid depending on the use of device 10. For example, in cases where device 10 is used to steer an endoscopic camera, device body 12 can be hollow in order to enable routing of wires or fiber optic cables from a user operable end (handle) to a camera or lens mounted on a distal end of elongated device body. A hollow device body 12 can also be used to route wires for controlling an operation of a tissue manipulator head such as a grasper and/or for accommodating at least one elongated elastic element for providing device body with elastic rigidity (further described hereinbelow).

Device 10 also includes a user operable interface 18 attached to proximal end of device body 12 and an effector end 20 (e.g. tissue manipulator such as a grasper) attached to a distal end of device body 12. Interface 18 functions in controlling and setting a orientation and position of elongated body 12, angling of steerable portion 14 and in operating effector end 20 (e.g. opening/closing, rotating and angling a grasper).

For example, in the configuration shown in FIG. 1a, a user 2 (e.g. surgeon) can press/release handles 300 to close and open the jaws of the grasper, rotate interface 18 in order to rotate the grasper jaws, and/or tilt housing 400 in order to deflect steerable portion 14. These actions can be done separately or simultaneously.

An interface 18 that can be used with device 10 is further described hereinbelow. Alternatively, the device 10 can incorporate the interface described in U.S. Provisional Patent Application No. 61/694,865, the contents of which are fully incorporated herein.

Figure 2:
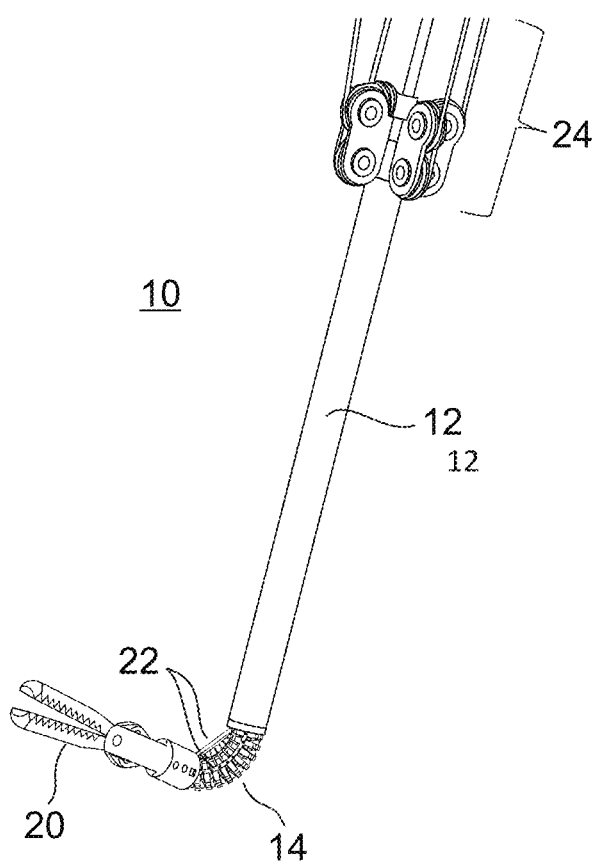
FIG. 2 illustrates the elongated body (fitted with grasper end) and the drive unit components of the device of FIGS. 1a-1h.

FIG. 2 illustrates routing of control wires 22 from drive unit 24 to a point distal to steerable portion 14. Drive unit 24 can include levers, pulleys and gears for translating hand movements of the user (control movements) to pulling of control wires 22. Such transfer can be mechanical (manual) or motorized. A motorized embodiment of drive unit 24 is further described in U.S. Provisional Patent Application No. 61/872,727.

In the embodiment shown in FIG. 2, control wires 22 are routed within device body 12 (e.g. under a sheath covering device body 12 or in the tube) up to steerable portion 14. At steerable portion 14, control wires 22 (one shown) is free from device body 12, such that angulation of steerable portion deflects control wire 22 away from the longitudinal axis of device body 12. Deflection of the control wire away from the longitudinal axis of the device (radially outward) increases the offset between the control wire and the deflection axis of the elongated device body and thus minimizes the pulling force needed to achieve deflection.

Figure 3B:
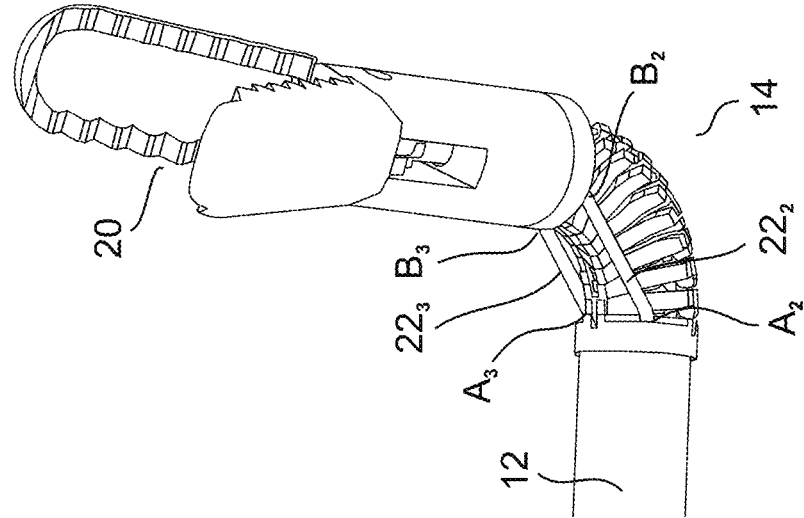
FIGS. 3a-3b illustrate one embodiment of a steerable potion of the present device.
Figure 3A:
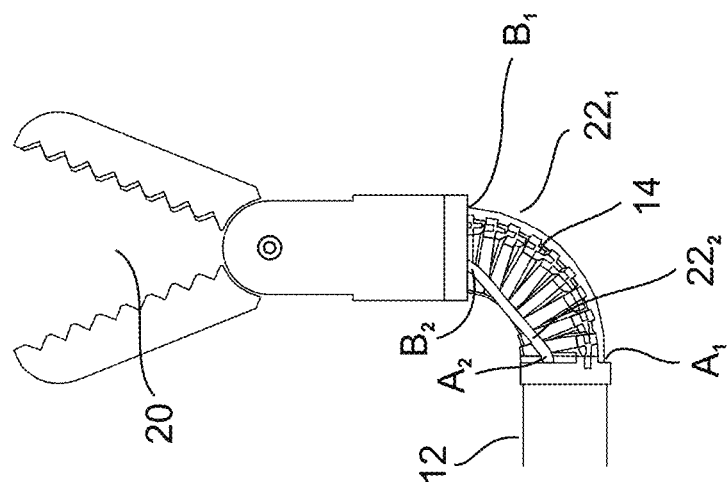

Steerable portion 14 (composed of links) is shown in greater detail in FIGS. 3a-4b. In FIGS. 3a-3b, control wires $22_2$ $22_3$ are attached to distal end of articulation 14 at point $B_2$, $B_3$ and routed into body 12 through point $A_2$, $A_3$. In between, control wires $22_2$ $22_3$ are free to move away from device body 12 and thus deflect away from device body 12 when pulled to angle steerable portion 14. FIG. 3a illustrates pulling of control wires $22_2$ $22_3$, control wire $22_1$ is not pulled and thus remains flush against device body 12. Pulling of control wires $22_2$ $22_3$ deflects effector end 20 (grasper shown) in the plane between control wires $22_2$ $22_3$. FIG. 3b illustrates simultaneous pulling of control wires $22_2$ $22_3$. Both control wires deflect away from device body 12 (at steerable portion 14) and pull effector end 20 in a plane between control wires $22_2$ $22_3$ resulting in angling of effector end 20.

Figure 4B:
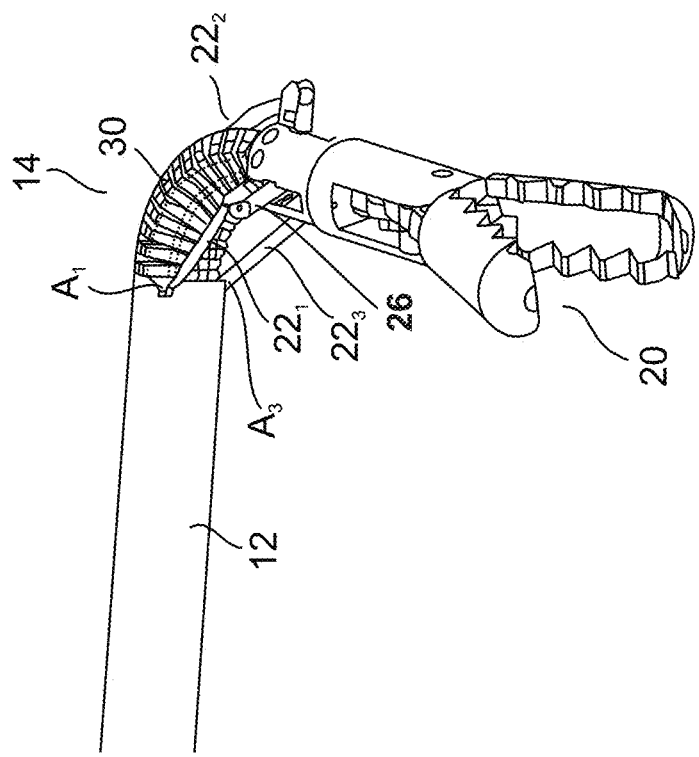
FIGS. 4a-4b illustrate another embodiment of a steerable potion of the present device.
Figure 4A:
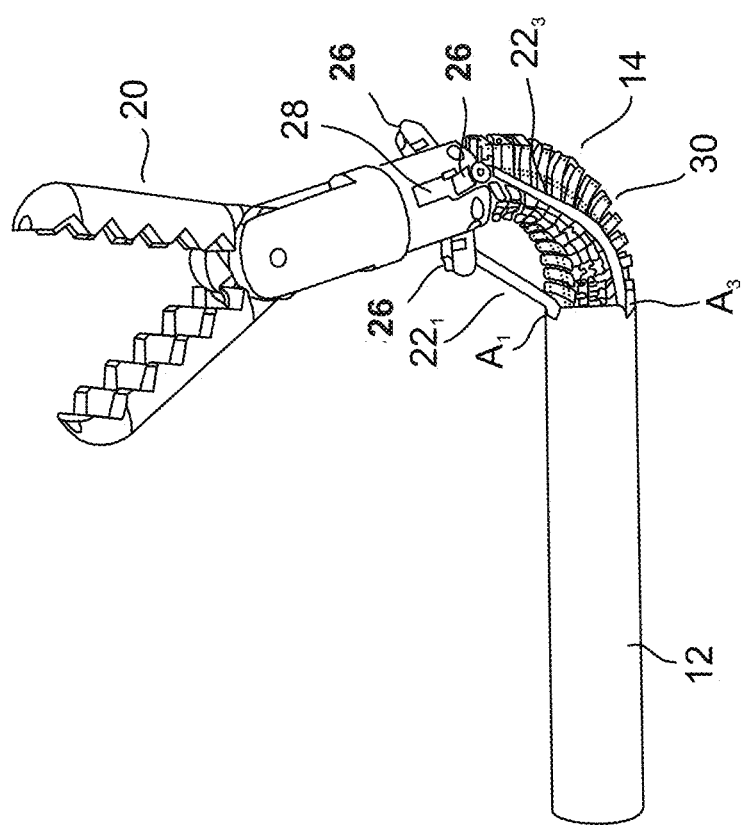

In the embodiment of FIGS. 3a-3b, control wires $22_2$ $22_3$ and $22_1$ are attached directly to distal end of articulation 12 at $B_1$ $B_2$ $B_3$ and routed into body 12 through $A_1$ $A_2$ $A_3$. In FIGS. 4a-4b, control wires 22 are attached to retractable levers 26 at a distal end thereof. Levers 26 are disposed within slots 28 in device body 12 when device 10 is delivered into the body. Levers 26 can be spring loaded and sequestered within slots 28 during delivery through a port. Once the region of device body 12 containing levers 26 exits the port (i.e. is free of the radial constraints imposed by the port inner wall), levers 26 can spring out; alternatively, levers 26 can fold out when control wires 22 are pulled. In any case, once deployed, levers 26 deflect the distal ends of control wires 22 away from device body thus increasing leverage of control wires 22 and further reducing the pulling force needed to deflect steerable portion 14. When device body 12 is pulled out of the body through a port, levers 26 collapse into slots 28 to facilitate removal through the port.

Figure 5C:
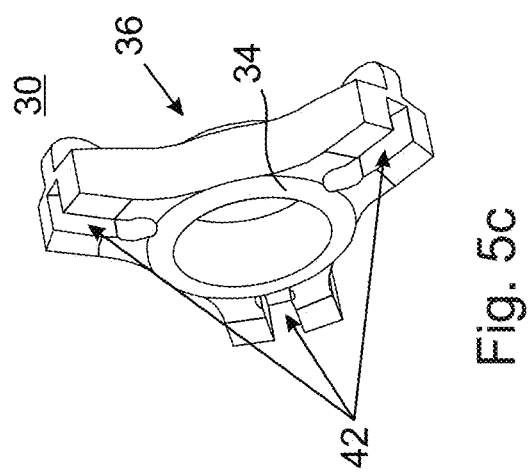
FIGS. 5a-5d illustrate one embodiment of a link utilizable for constructing a steerable portion of the present device (FIGS. 5a-5c), and a steerable portion constructed from a plurality of links.
Figure 5A:
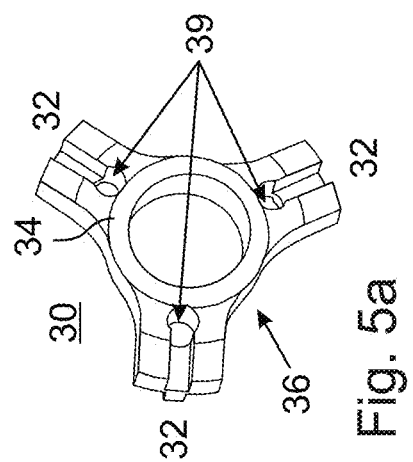
Figure 5B:
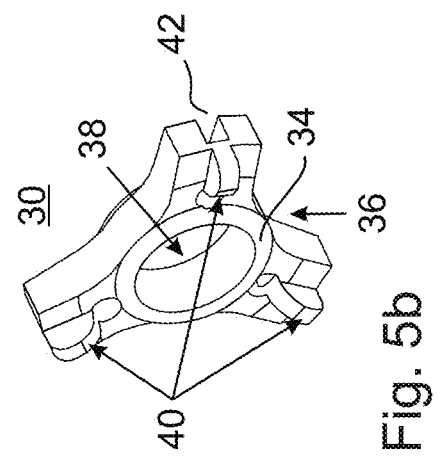

As is mentioned hereinabove, one embodiments of device body 12 or at least steerable portion 14 is preferably constructed from a series of links. FIGS. 5a-5c illustrate one embodiment of links 30 with assembly of links 30 into steerable portion 14 illustrated in FIG. 5d.

Figure 5D:
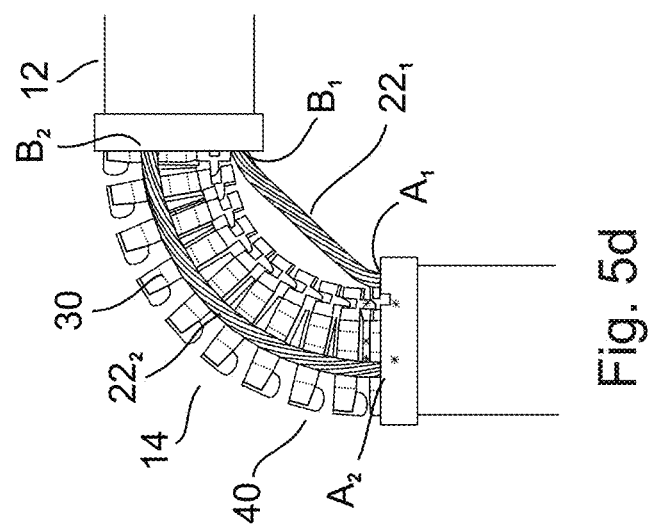
Figure 6:
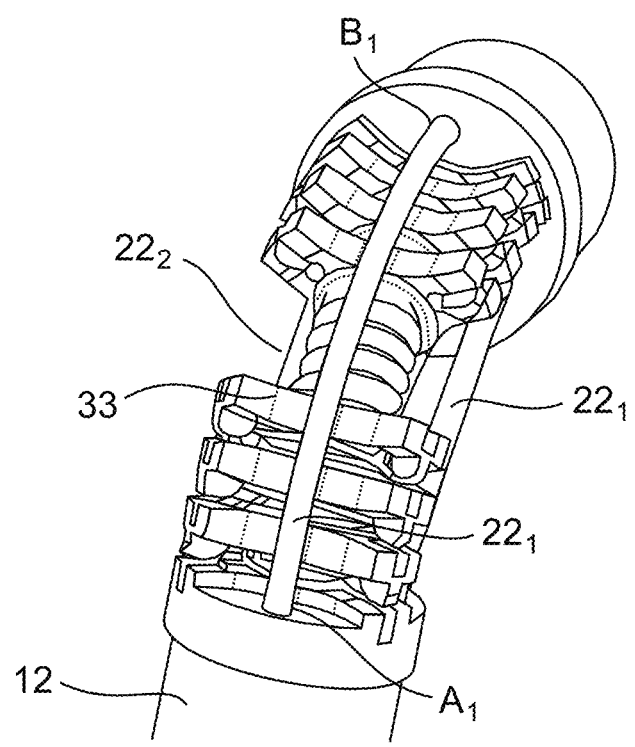
FIG. 6 illustrates a steerable portion with several links removed exposing the spring element fitted within a central core of the links.

Links 30 preferably include several arms 32 (3 shown) mounted around a central hub 34. As is shown in FIG. 5d, the inter-arm space 36 accommodates control wires 22, and thus the number of arms 32 (preferably 2-12) dictates the number of control wires 22 used in device 10.

Link 30 is preferably fabricated from an alloy or polymer via machining molding or the like.

Hub 34 includes a central circular opening 38 (FIG. 5b), while each arm 32 optionally includes an opening 38 (FIG. 5a). Opening 38 can accommodate an elongated elastic element (e.g. spring coil 33 shown in FIG. 6 or an elastic tube) for interlinking links 30 and providing device body 12 with rigidity and elasticity at steerable portion 14. Openings 39 can be used to route wires for actuating effector end or for accommodating elastic rods (as an alternative to one central rod mounted through opening 38. Openings 39 can also be used to route electrical wires to operate a motor or a camera or jaws of a grasper or any other sensor or actuator at a point distal to steerable portion 14. Opening 38 can also serve as a through lumen for delivering an irrigation tube, optical fibers and the like.

In order to prevent or limit rotation of links 30 when control wires 22 are pulled, each link includes tabs 40 and slots 42 on opposite faces. Preferably each arm 32 includes a tab 40 and an opposing slot 42 although the length and width can vary between arms 32 of a single link 30. Tabs 40 of a link 30 are capable of engaging slots 42 of an adjacent link 30, thus limiting relative rotation of links 30.

The configuration and positioning of tabs 40 and slots 42 can be selected so as to completely limit rotation, or limit rotation to a specific angle range (5-15 degrees) or a specific direction etc. In any case, the engagement between tabs 40 and slots 42 can be reversible thus allowing disengagement therebetween when steerable portion 14 is deflected and links 30 angle with respect to each other.

FIGS. 7a-7h illustrate another embodiment of links 30, which can be stacked as shown in FIGS. 7a-7c to form steerable portion 14.

Links 30 of this embodiment of device 10 are roughly disc-shaped and include a central opening 50, a plurality of circumferential openings 52 (FIGS. 7d-7g), indents 54 (FIGS. 7e, 7g, 7h) and depressions 56 (FIGS. 7d, 7f).

Central opening 50 serves for routing one or more wires from the device handle to effector end 20. Such wires actuated by the handle to control effector end 20 (e.g. open, close, rotate grasper). Circumferential openings 52 serve for routing control wires 22 for actuating deflection of steerable portion 14. Indents 54 and depressions 56 interconnect adjacent links 30 and enable such links to angle with respect to each other. An elastic rod or tube or spring can be positioned through central opening 50 to provide elasticity to links 30.

Figure 8C:
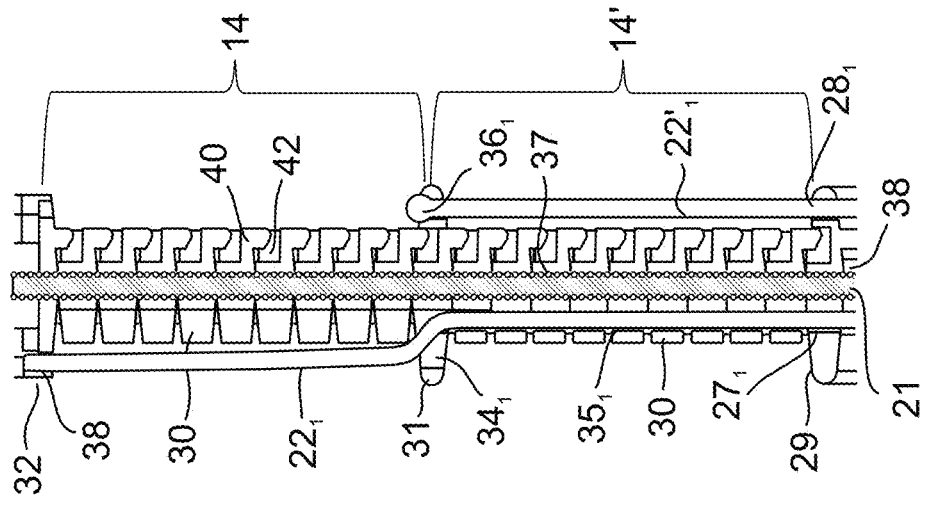
FIGS. 8a-8q illustrate an embodiment of the present device that includes two offset steerable portions deflectable to form, for example, U-shaped (FIG. 8k) and S-shaped (FIG. 8l) articulation configurations.
Figure 8B:
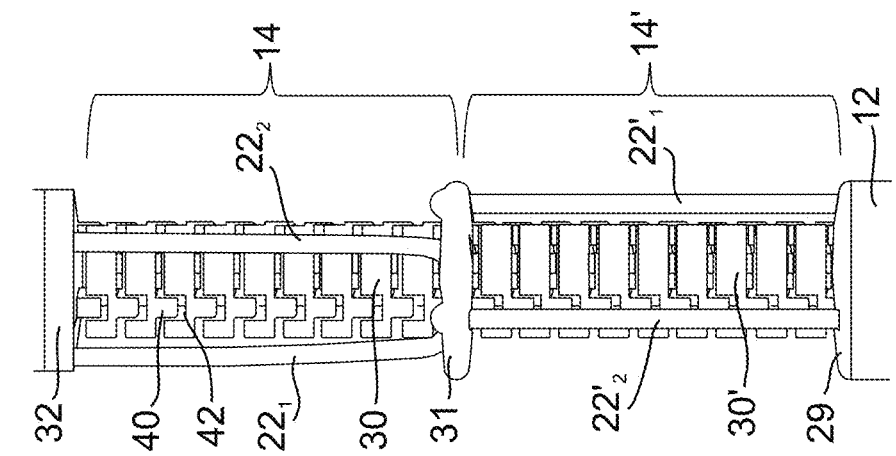
Figure 8A:
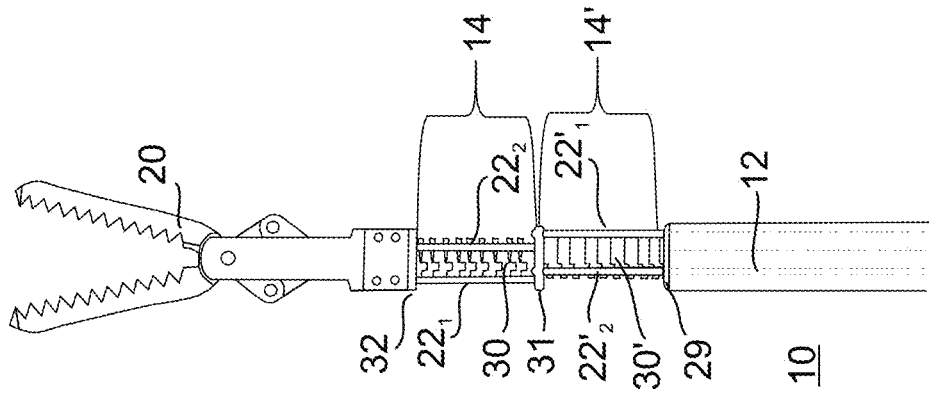

FIG. 8a illustrates an embodiment of device 10 which includes two independent steerable portions: 14 and 14'. Device 10 includes a device body 12 (also referred to herein as shaft 12) with a typical diameter of 5-12 mm. The distal end of device body 12 is fitted with an effector end 20 which can be, for example, a grasper as shown in this Figure. Steerable portion 14' includes a proximal base link 29 which is connected to the distal end of shaft 12, a series of links 30 and a distal end link 31. Distal ends of control wires $22'_{1,2,3}$ are connected to link 31, while the proximal ends of these wires are connected to a drive unit 24 (FIG. 2) which is operated from the handle.

Control wires $22_{1,2,3}$ are connected to distal link 32 of steerable portion 14, and are routed through link 31 and the bodies of links 30' to drive unit 24 (FIG. 2) which is operated from the handle.

FIG. 8b illustrates steerable portions 14 and 14' in greater details. Each of steerable portions 14 and 14' includes 9 identical links (30 and 30'), however, different number of links of different geometry can be used in each steerable portion. Tabs 40 and slots 42 (described hereinabove with respect to FIGS. 5a-5d) of links 30 and 30' are also shown.

FIG. 8c is a cross sectional view of steerable portions 14 and 14'. Flexible shaft 21 (connected to drive unit 24 at its proximal end) is positioned through holes 38, 37 of links 29, 30', 30, 31 and 32, the distal end of flexible shaft is connected to effector 20.

Control wire 22'1 passes through hole $28'_1$ of link 29 and hole $36'_1$ of link 31; distal end of control wire $22'_1$ is connected to link 31 to/in hole $36'_1$; control wire $22'_1$ is routed out of links 30'. Control wire $22_1$ passes through hole $27_1$ of link 29 and through hole $35_1$ of links 30' (shown in detail in FIG. 8d). At link 31, control wire $22_1$ deflects out through elongated opening $34_1$ of link 31 and runs out of links 30 to a distal connection point 38 at link 32. Control wires 22'2 and 22'3 are similar in routing and attachment to control wire $22'_1$, while control wires $22_2$ and $22_3$ are similar in routing and attachment as control wire $22_1$.

Figure 8F:
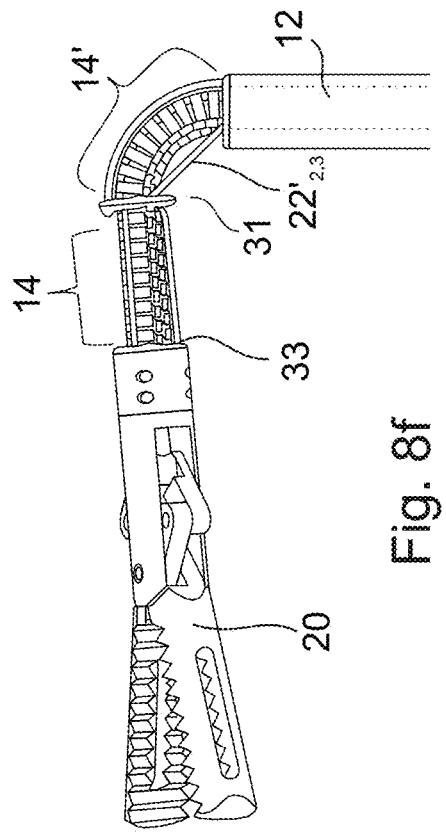
Figure 8G:
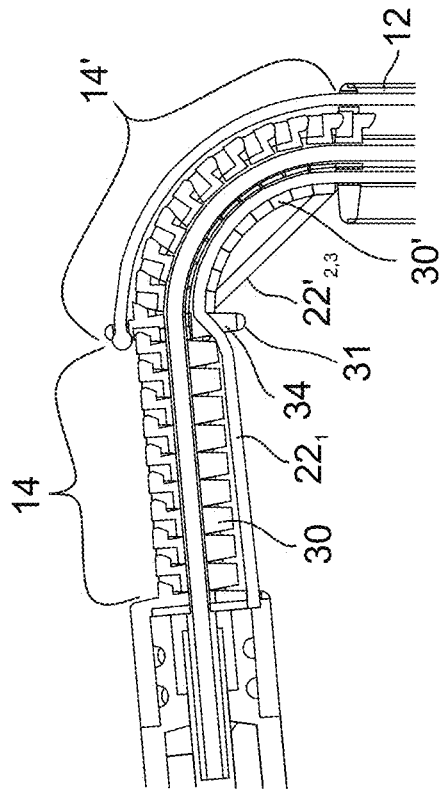
Figure 8D:
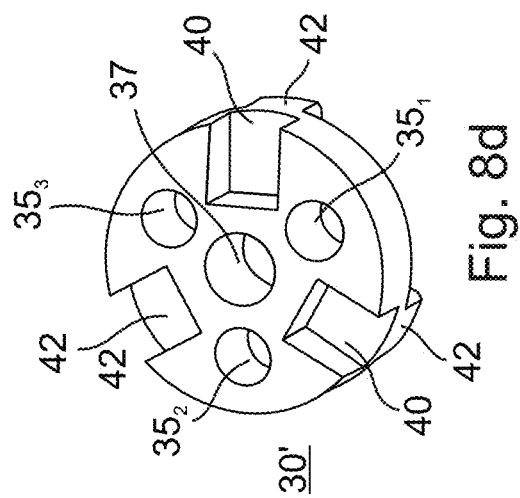

FIG. 8d illustrates link 30' in detail. Central hole 37 accommodates flexible shaft 21 while holes $35_{1,2,3}$ accommodate control wires $22_{1,2,3}$ (tabs 42 and slots 40 are also shown).

Figure 8E:
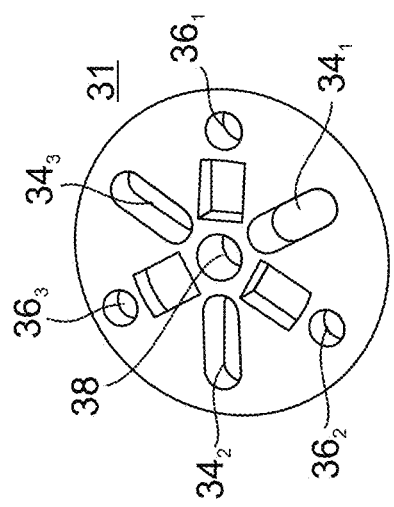

FIG. 8e illustrates link 31 in detail. Central hole 38 accommodates flexible shaft 21 while holes $36_{1,2,3}$ serve as connection points for control wires $22'_{1,2,3}$. Elongated openings $34_{1,2,3}$ route control wires $22_{1,2,3}$ out of links 30.

Deflection of portions 14 and 14' and thus steering and articulation of shaft 12 is effected via pulling forces on control wires $22_{1,2,3}$ and $22'_{1,2,3}$. If a control wire is close to the center of a steerable portion, such as the case with control wires $22_{1,2,3}$ which run through holes $35_{1,2,3}$ in steerable portion 14', then a pulling force on these control wires results in a relatively small deflection, in other words the effect of a pulling force on deflection is in direct relationship to the distance between control wire $22_{1,2,3}$ to a center of a steerable portion 14. When a control wire 22 is connected to a distal end of a steerable portion 14 and is free to move through the proximal base, e.g. when threaded through holes $34_{1,2,3}$ in link 31, then the effect of a pulling force on steerable portion 14 is enough to deflect it from the longitudinal axis. This effect of the pulling force increases as steerable portion 14 deflects since control wire 22 bows outward (radially) and the distance between the control wire 22 and center of steerable portion 14 increases.

FIG. 8f illustrates a configuration capable of an 80 degree deflection, i.e. effector end 20 can assume an angle of 100 degrees with respect to the longitudinal axis of shaft 12. Deflection of proximal steerable portion 14' is effected by pulling (in a proximal direction) on control wires $22'_{2,3}$.

FIG. 8g is a cross sectional view of the device of FIG. 8f showing routing of control wires 22. A prototype constructed in accordance with the configuration of FIGS. 8f-8g is shown in FIG. 10b.

Figure 8I:
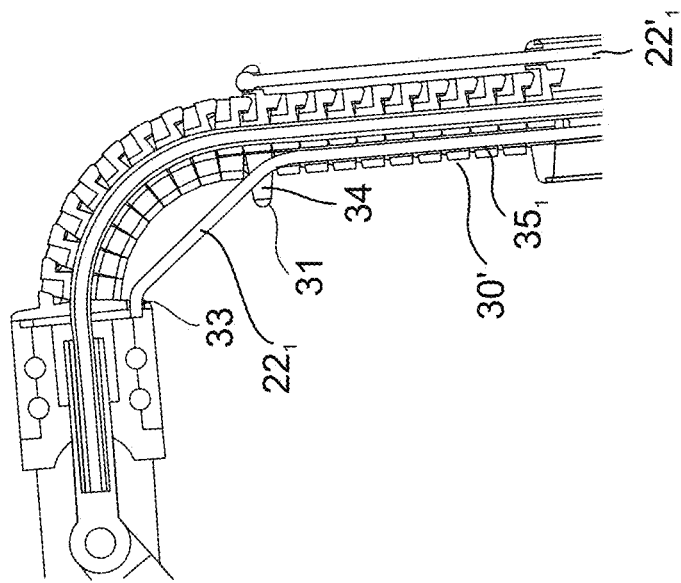
Figure 8H:
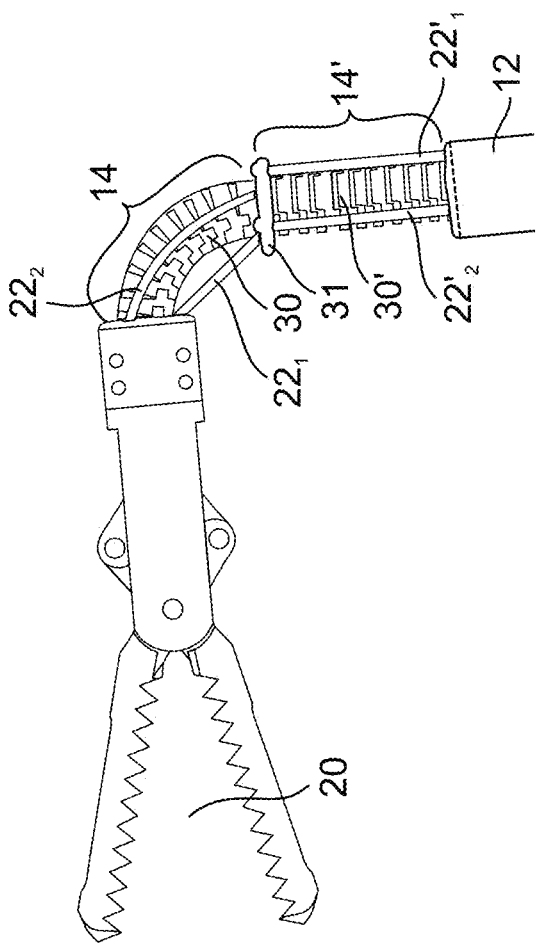

FIG. 8h illustrates a configuration capable of an 80 degree deflection, i.e. effector end 20 can assume an angle of 100 degrees with respect to the longitudinal axis of shaft 12. Deflection of distal steerable portion 14 is effected by pulling (in a proximal direction) on control wire $22_1$.

FIG. 8i is a cross sectional view of the device of FIG. 8h showing routing of control wire $22_1$. Control wire $22_1$ runs through hole $35_1$ in links 30' of steerable portion 14' and as such its distance from the center of steerable portion 14' is minimal. This small distance, ensures that the pulling forces applied on control wire $22_{1,2,3}$ will have little or no effect on the deflection of steerable portion 14'. At the distal end of proximal steerable portion 14', control wire $22_1$ runs through elongated opening $34_1$ in link 31 and connects to link 32 at point 3'71. This direct connection positions control wire $22_1$ outward from the center of steerable portion 14, and therefore increase the moment arm of the pulling force. This enables steerable portion 14' to deflect (bend) under relatively small pulling forces.

Figure 8J:
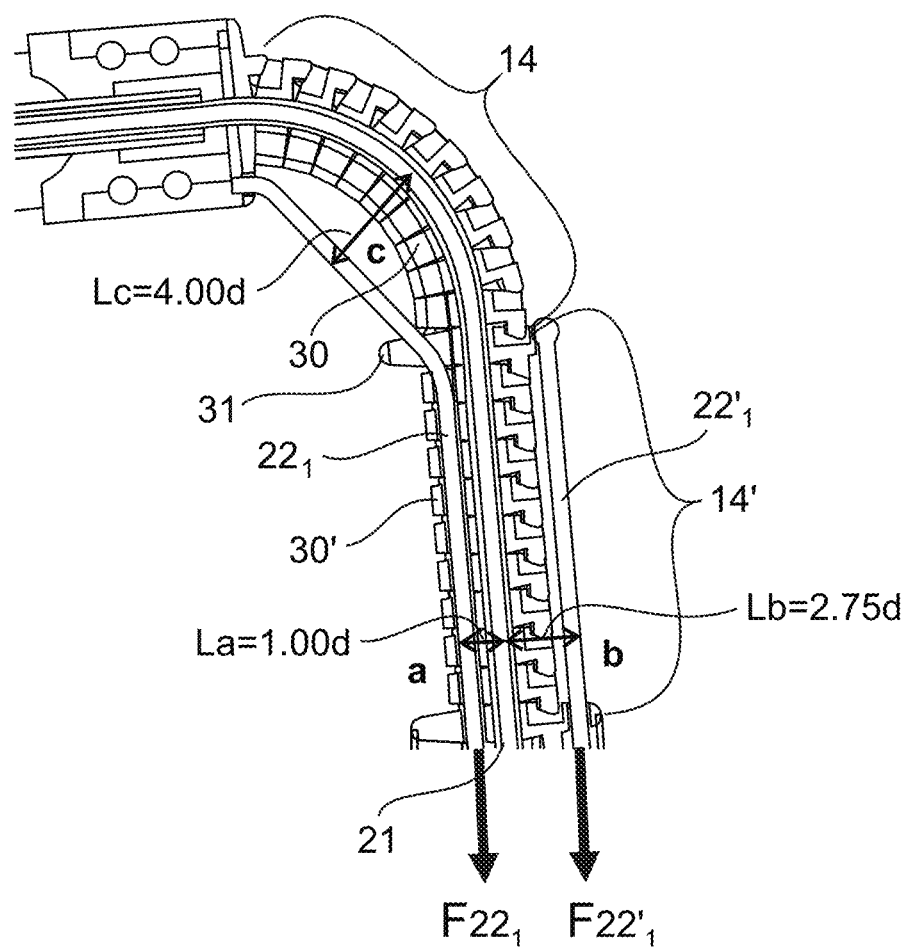

FIG. 8j illustrates routing of control wires $22_1$ and $22'_1$ and central flexible shaft 21 and the effect of wire routing on deflection forces. In this Figure, "d" represents 1 unit of distance, in this case, the distance between the center of hole $35_1$ to the center of link 30'. The following parameters are used for calculations:

"a"—measurement of the longest arm moment of control wire $22_1$ from the center point of link 30'. La=1.00d;

"b"—measurement of the longest arm moment of control wire $22'_1$ from the center point of link 30', Lb=2.75d;

"c"—measurement of the longest arm moment of control wire $22_1$ from the center point of link 30, Lc=4.00d.

A force $F22_1$ is applied to control wire $22_1$, thus the moment force $F22_1$ applies on portion 14' is:

$$Ma = F22_1 \times La$$

$$Ma = F22_1 \times 1.00d$$

The moment the force $F22_1$ applies on portion 14 is:

$$Mc = F22_1 \times Lc$$

$$Mc = F22_1 \times 4.00d$$

The moment applied by on portion 14 compared to the moment applied on portion 14" by the same force $F22_1$ is:

$$Mc/Ma = F22_1 \times 4.00d / F22_1 \times 1.00d = 4$$

The above calculations when applied to commercially available devices, illustrate that the present invention can reduce the wire pulling force needed for deflection by at least 25% when compared to such commercially available devices (see Examples section for further detail).

The bending moment on steerable portion 14 (the "target steerable portion") caused by force ($F22_1$) applied by control wire $22_1$ is significantly greater than the bending moment on steerable portion 14' (the "secondary steerable portion"), and as such, a coupling effect between these two steerable portions is minimized.

Minimizing such coupling enables the use of a simple mechanism, such as hand operated mechanism, to steer the articulation without the need to add a controller to the control wires mechanism.

When using an electro-mechanical mechanism to pull the control wires then the moments on the secondary portion may be reduced to zero by using a controller that is programmed to apply force on control wire $22'_1$. The magnitude of this force may be calculated by:

$$Ma = Mb \text{(canceling moments)}$$

$$Ma = F22_1 \times La = F22_1 \times 1.00d$$

$$Mb = F22'_1 \times L = F22'_1 \times 2.35d$$

$$F22_1 \times La = F22_1 \times 1.00d = F22'_1 \times L = F22'_1 \times 2.35d$$

$$F22'_1 = F22_1 \times 1.00d / 2.35d$$

$$F22'_1 = 0.42 F22_1$$

As calculated the controller will operate the actuator that pulls control wire $22'_1$ in a force less than a half of force $F22_1$ ($F22'_1 = 0.42 F22_1$).

It will be appreciated that in cases where an electro-mechanical drive unit is used for pulling the control wires, than the control wires routing described above can reduce the energy consumption of the motors controlling the first and second steerable portions.

Figure 8K:
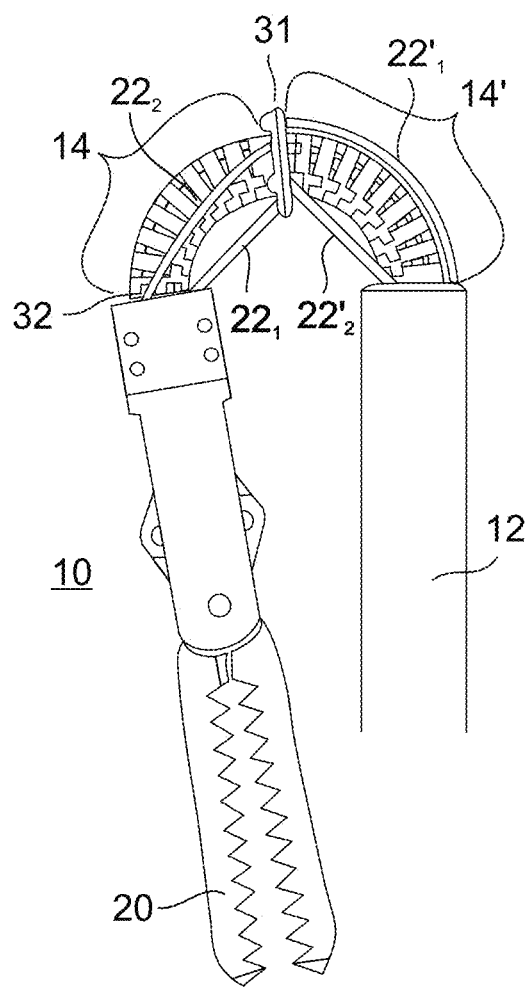

The routing principles described hereinabove may be used in any combination to deflect two or more steerable portions and generate any articulation desired. For example, FIG. 8k illustrates "U"-shaped articulation with effector end 20 positioned at an angle of 190 degrees. Such articulation is achieved by pulling control wires $22'_1$ and $22_2$.

Figure 8L:
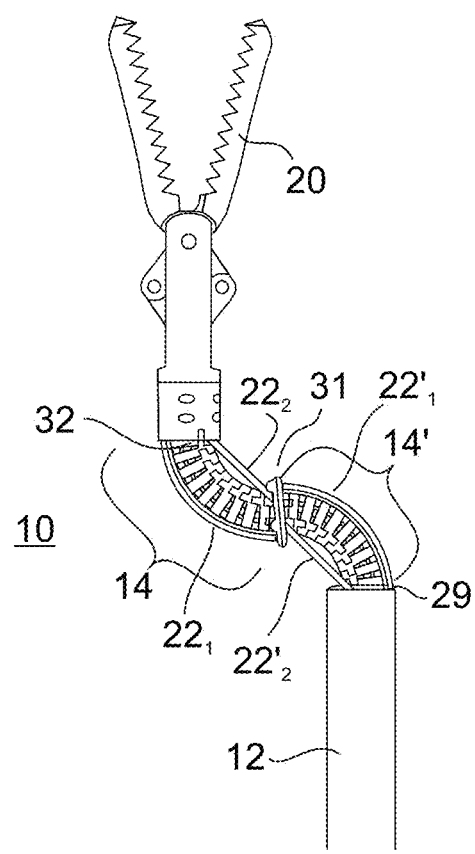

FIG. 8l illustrates an "S"-shaped articulation which can be achieved by pulling control wires $22'_1$ and $22_1$.

Figure 8P:
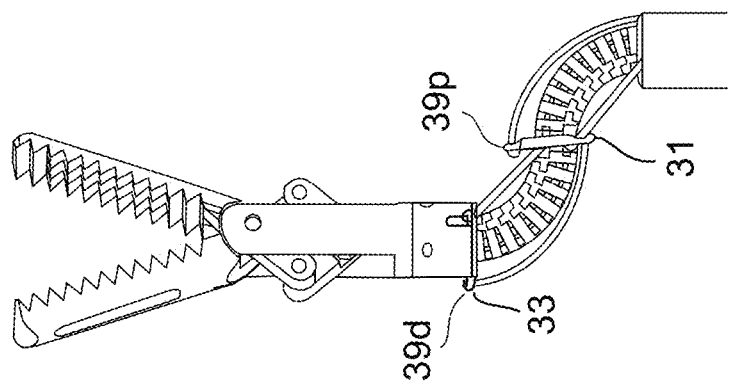
Figure 8O:
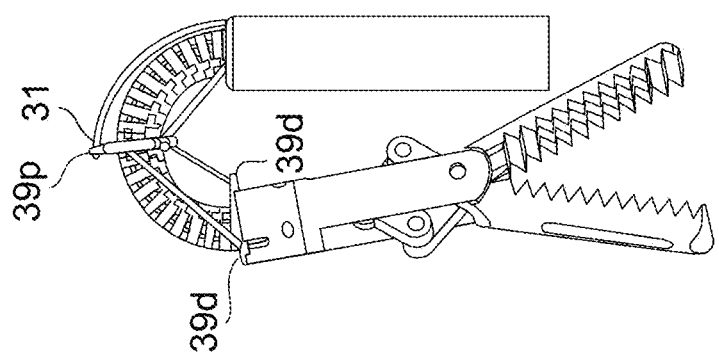
Figure 8N:
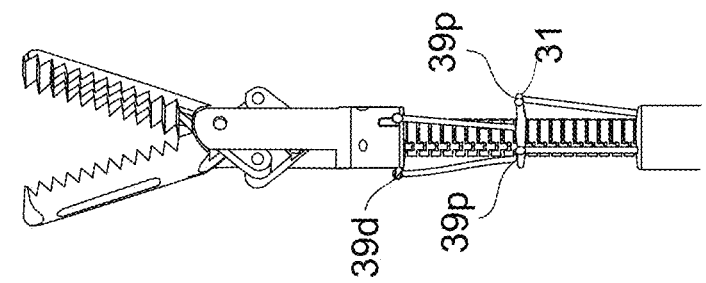
Figure 8M:
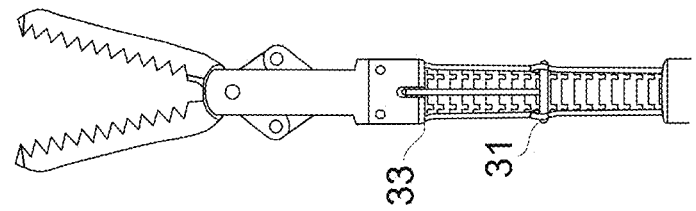

FIGS. 8m-8p illustrate a device having two steerable portions with deployable arms positioned at a distal end of each steerable portion. Arm 39p is hingedly connected to link 31 and arm 39d is hingedly connected to link 33. Arms 39p and 39d can swing outward and increase the distance between the end of a control wire connected thereto and the center of the deflectable portion. FIG. 8m illustrates arms 39p and 39d in a folded position, FIG. 8n illustrates arms 39d and 39p in an open position. FIG. 8o illustrates "U"-shaped articulation with arms 39d and 39p in an open position. FIG. 8p illustrates "S"-shaped articulation with arms 39d and 39p in an open position.

Figure 8Q:
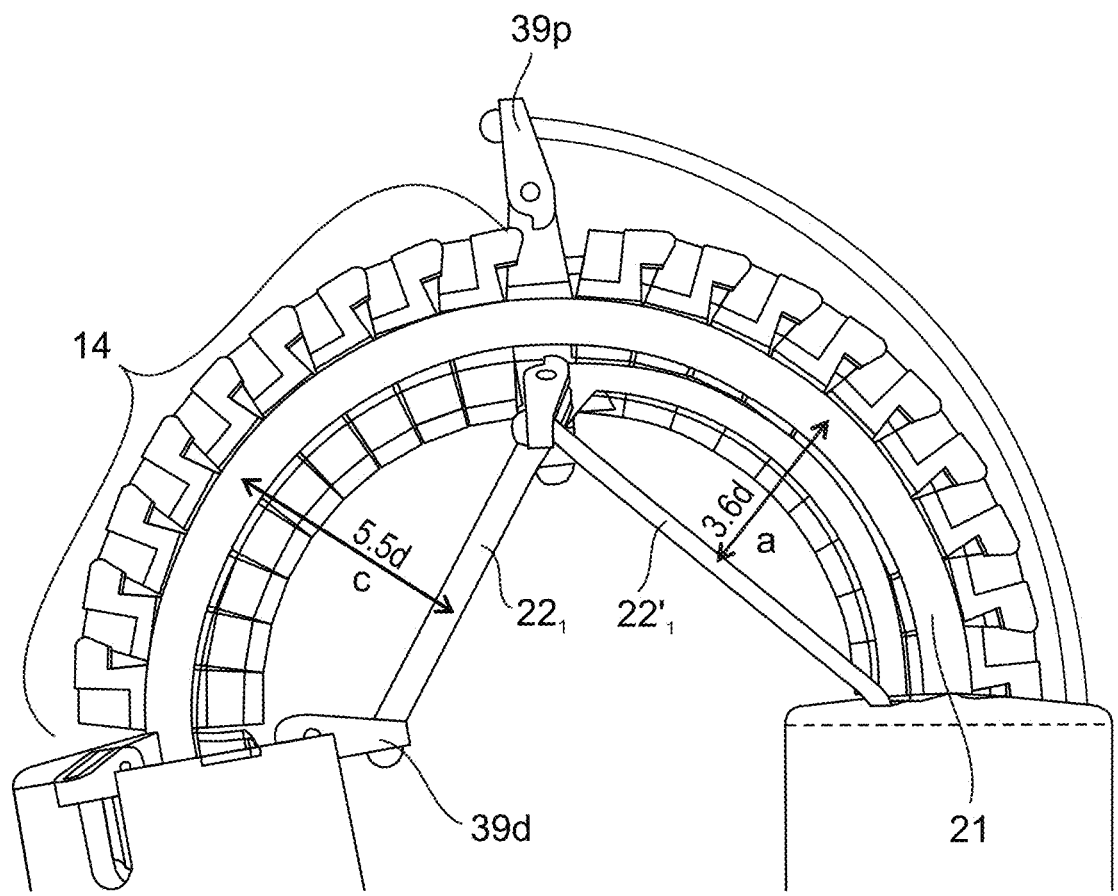

FIG. 8q is a cross sectional view of the present device in a "U"-shaped configuration with arms 39d and 39p in an open position. In this example arms 39p and 39d have the same dimensions. The moment arm of control wire $22_1$ attached to arm 39d is 5.5d.

The effect of using arms 39d and 39p on the force needed to deflect the steerable portion can be represented by the following calculation:

$$\text{Device with no arms: } Mc = F22_1 \times 4.00d$$

$$\text{Device with arms: } M_{arms}c = F_{arms}22_1 \times 5.50d$$

$$M_{arms}C = Mc$$

$$F22_1 \times 4.00d = Farms22_1 \times 5.50d$$

$$F_{arms}22_1 = F22_1 \times 4.00d/5.50d$$

$$Farms22_1 = F22_1 \times 4.00d/5.50d$$

$$F_{arms}22_1 = 0.73 F22_1$$

The foregoing describes examples of device 10 capable of single plane articulation, however it will be appreciated that device 10 having two or more steerable portions can be deflected to form a multi-planar articulated configuration such as that shown in FIG. 10c or even a complete loop. Such multi-planar articulation can be achieved by actuating control wires which are located at different planes or by for example applying non symmetrical forces on pairs of control wires.

As is mentioned herein above, any handle and mechanism can be used with device 10 of the present invention. The construction and operation of one embodiment of a handle utilizable with the present device is illustrated in FIGS. 1b-1h. FIGS. 1b-1c illustrate grasper head 20 and steerable portion 14 which is actuatable via the device handle interface (18) and its internal mechanism. In this embodiment the steerable portion is controlled by 4 control wires 22. Steerable portion 14 is shown deflected in a direction of pulled control wire $22_2$.

Figure 1E:
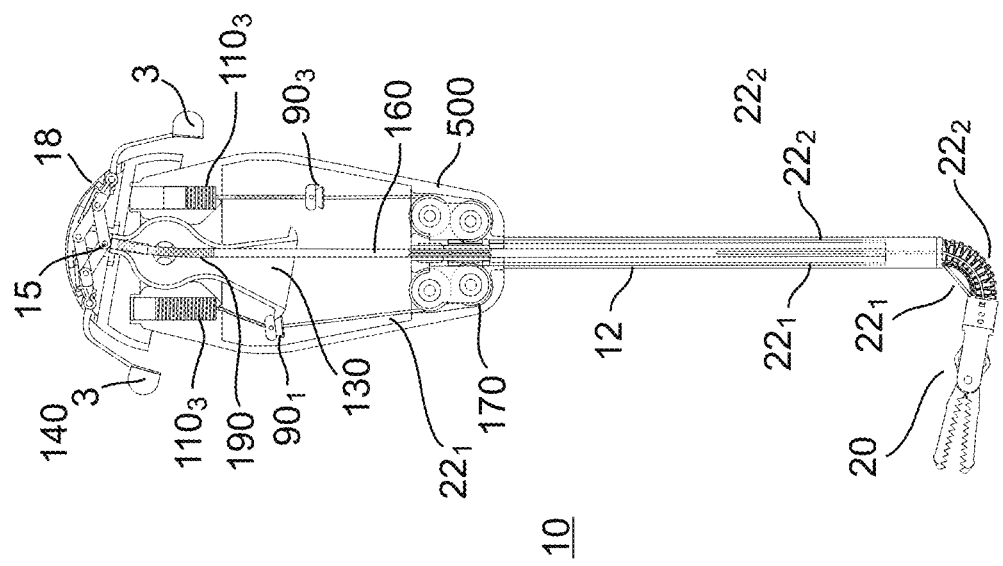
Figure 1D:
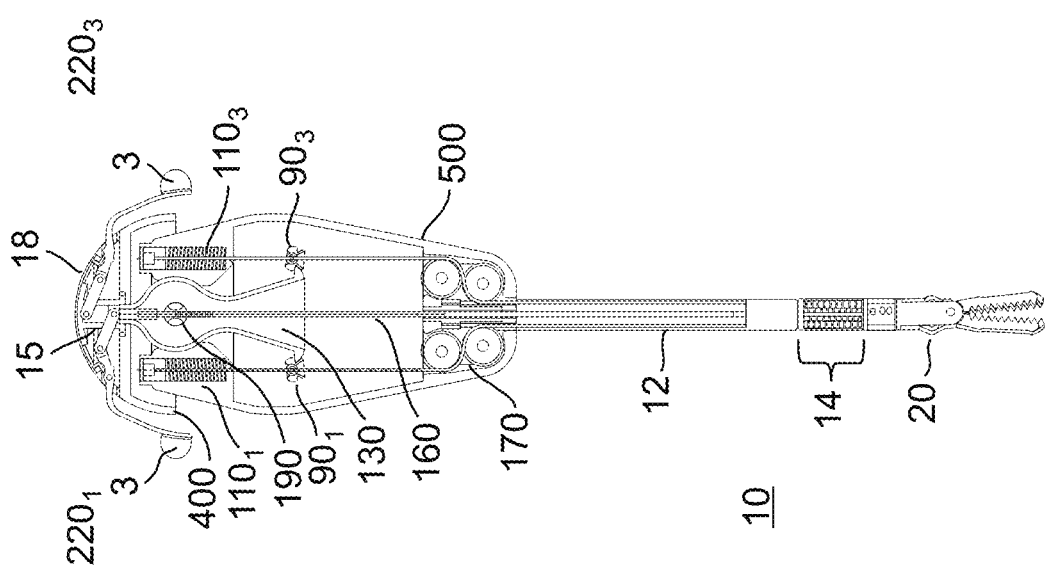
Figure 1H:
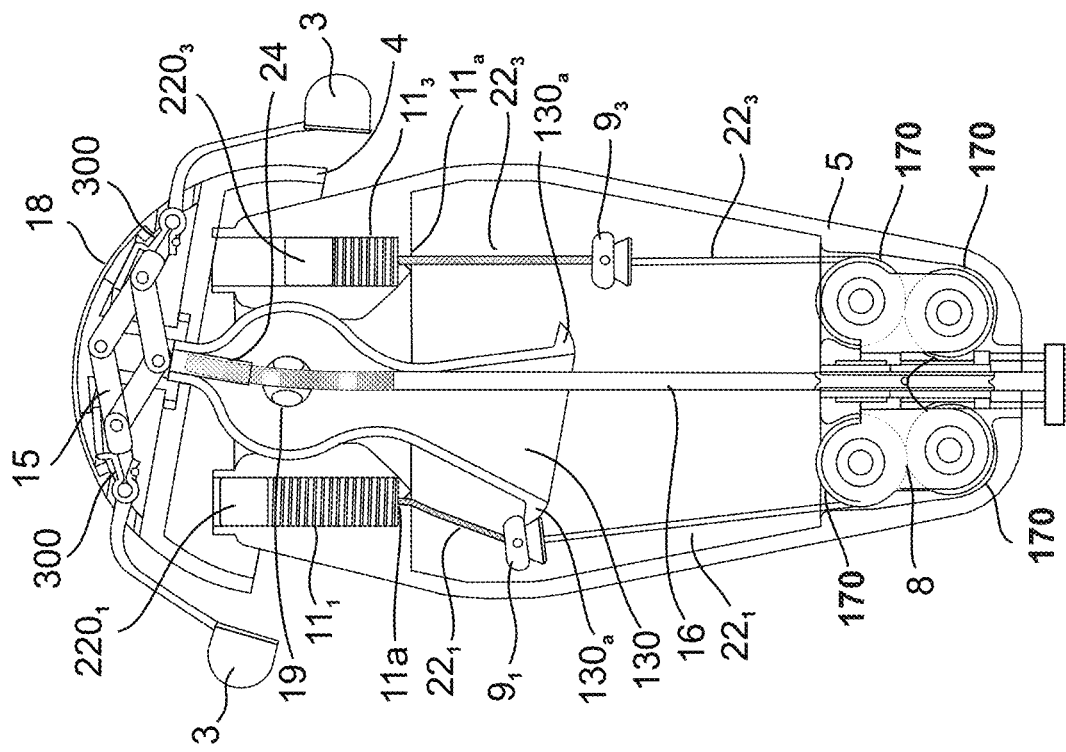
Figure 1G:
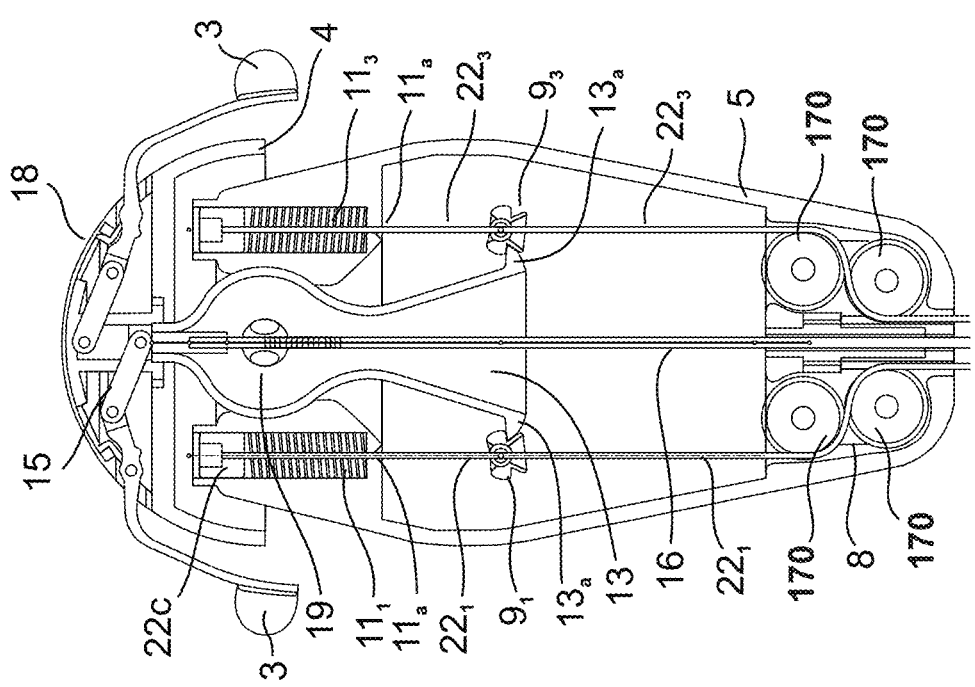

FIGS. 1d-1e and 1g are cross sectional views of device 10 showing the mechanism in the handle that enables transfer of interface movements to the control wires.

The grasper jaws are actuated via mechanism 15 via cable 160. Control wires 22 (22 1, 22 2, 22 3, 22 4) which are attached to a distal end of steerable portion 14, are routed via a pair of pulleys 170 to a hole at the base of springs $110_{1,2,3,4}$ of housing 500. Control wires $22_{1,2,3,4}$ are prevented from slipping through springs $110_{1,2,3,4}$ by crimps $220_{1,2,3,4}$. The shape of crimps $220_{1,2,3,4}$ follows the shape of the housing of spring 110 to ensure smooth and predictable movement of a compressed springs $110_{1,2,3,4}$ when a control wire $22_{1,2,3,4}$ is pushed away from center by body 130.

Body 130 is connected to housing 500 by ball joint bearing. Body 130 is located at the center of the mechanism, and may be tilted with respect to housing 500, by forces applied on interface crown 400 by a user. Control wires $22_{1,2,3,4}$ surround body 130, when body 130 is in a neutral position each control wire $22_{1,2,3,4}$ is pressed against the circumferential edge of body 130 by slot 90a1,2,3,4 of bead $90_{1,2,3,4}$.

FIG. 1f illustrates the relationship between bead 90, control wire 22 ($22_1$ shown) and body 130 in detail. Bead 90 is connected firmly to control wire $22_1$ and divides control wire 22 into 2 contiguous regions: upper region $22_{1u}$ and lower region $22_{1d}$. Bead 90 includes a slot 90a that fits into the circumferential edge 130a of body 130.

FIG. 1h, illustrates in details the control mechanism, shown in a tilted position, with control wire $22_1$ pushed via bead $90_1$ away from center in order to deflect steerable portion 14. The engagement point between circumferential edge 130a of body 130 and bead $90_1$, is at the inner side of slot 90a. While body 130 pushes bead 90 away from the center, opposite-positioned bead $90_3$ is released from circumferential edge 130a. Control wire $22_3$ is connected at a distal end to an opposite side of control wire $22_1$. As seen in FIG. 1b, when steerable portion 14 is deflected by control wire $22_1$, the inner side of portion $14_{in}$ is shortened, and the length of $14_{out}$ at the opposite side of steerable portion 14 is increased. The length of wire $22_3$ must increase accordingly. Such length accommodation by control wire $22_3$ is possible by compressing spring $110_3$.

The grasper jaws are actuated via a mechanism 15 (FIGS. 1g-1h) which is controllable by the surgeon fingers. When handles 3 are pressed, the arms of mechanism 15 elevate piston 24 which closes the jaws. If the surgeon releases the force applied to handles 3, springs 300 which are connected to the arms of mechanism 15 push piston 24 back into body 500 and the jaws open. Piston 24 is connected to the jaws push/pull mechanism via flexible shaft 17 and tube 16. Flexible shaft 17 and tube 16 are used to transfer rotation and push-pull movement applied by mechanism 15. Flexible shaft 17 is bent in centering element 19 without changing its length, preventing an unwanted coupled movement of opening and closing of the jaws i.e. the grasper head and mechanism 150 does not move while steerable portion 14 is bent. The dimension of the inner side of body 130 is designed not to touch tube 160 when body 130 is tilted to extreme positions.

Although a steerable portion 14 constructed from interconnected links is advantageous in that it enables modular design, a steerable portion 14 constructed from a unitary flexible shaft is also envisaged herein.

A steerable portion constructed from a unitary flexible shaft is advantageous in that it simplifies construction and manufacturability. In addition, such a shaft is better at insulating central electrical wires, used, for example, in diathermia (monopolar or dipolar).

Figure 9A:
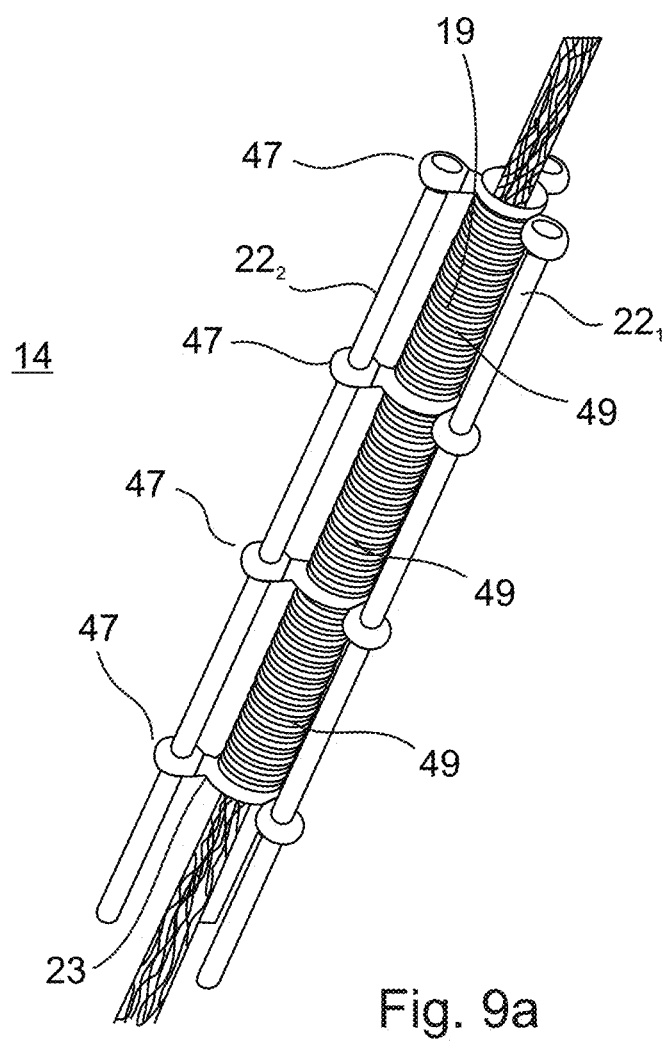
FIGS. 9a-9b illustrate an embodiment of the present device that includes a unitary flexible shaft fitted with guides for routing the control wires.
Figure 9B:
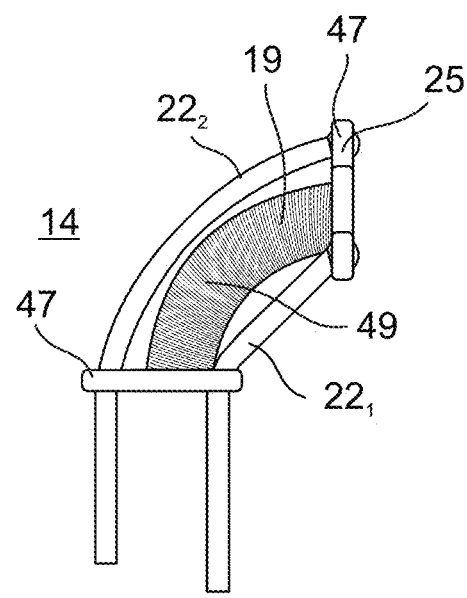
Figures 9C, 9D:
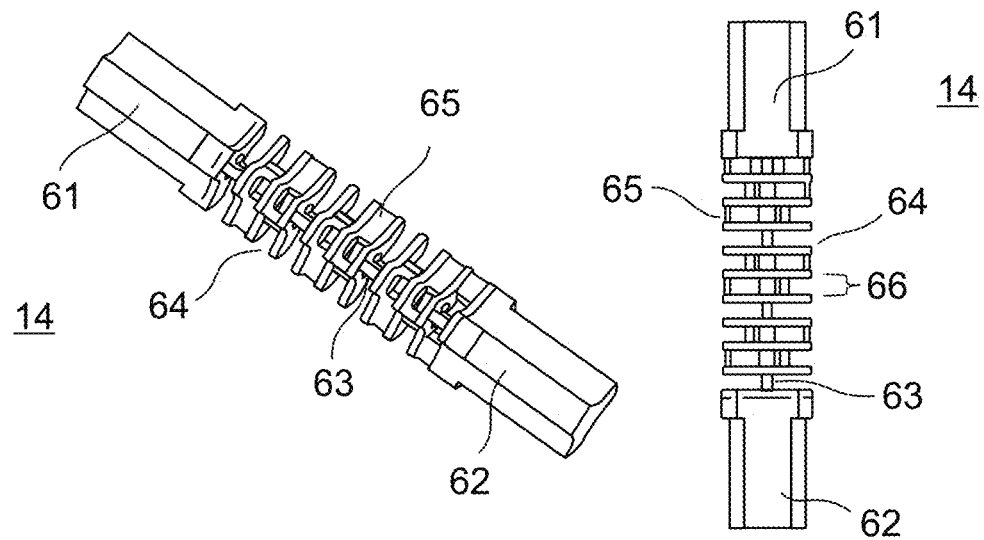
FIGS. 9c-9i illustrate another embodiment of the present device that includes a unitary flexible shaft including cutouts for enabling deflection.
Figure 9G:
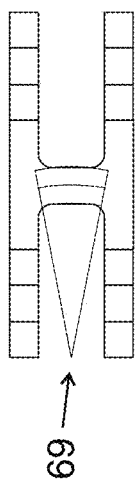

One example of such an embodiment of steerable portion 14 is shown in FIGS. 9a-9b.

Steerable portion 14 can include one or more steerable portions 49 (three shown in FIG. 9a) interposed between guides 47 attached along a length of a flexible shaft 19. Shaft 19 can be made of a tube fabricated from any elastic material including stainless steel, nitinol, rubber, silicon and is typically shaped as a solid or hollow cylinder with a diameter of 5-12 mm with wall thickness 0.1-0.5 mm. Steerable segments 15 can be 5-30 mm in length and guides 47 can be dimensioned to displace control wire 22 2-4 mm away from shaft 19. Guides are preferably configured with a central ring 23 for clamping around shaft 19 and several (e.g. 2-8) circumferentially attached rings 25 for routing of control wires 22.

Elasticity of shaft 19 ensures that steerable portion 14 or segment 49 deflect when specific control wire or wires 22 are pulled and linearize when control wire or wires 22 are released. Shaft 19 is selected so as to enable elastic deflection of one or more steerable portions 14 by 45 to 180 degrees.

Another embodiment of a unitary steerable portion 14 is shown in FIGS. 9c-9i.

This embodiment of unitary steerable portion 14 can be 5 mm in diameter (OD) with a central lumen of at least 1.4 mm. Unitary steerable portion 14 is constructed from a polymeric material (e.g. polyamide, polypropylene) that is capable of providing 90 degrees of elastic articulation (repeatedly) under a pulling force of 10 N (looping, spatial articulation) with a bending radius of about 7 mm. When a pulling force is released, an elastic force returns steerable portion 14 to a normal, linear configuration.

Figure 9F:
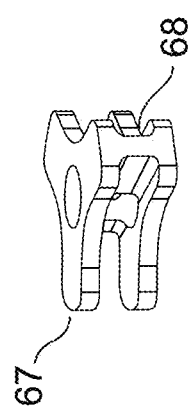
Figure 9I:
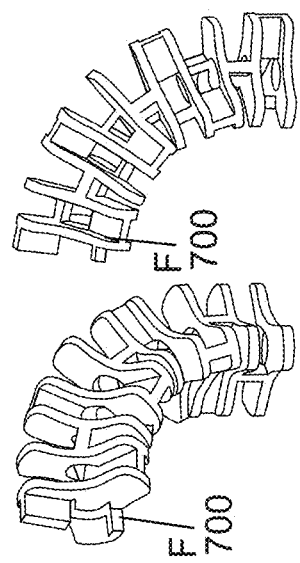
Figure 9E:
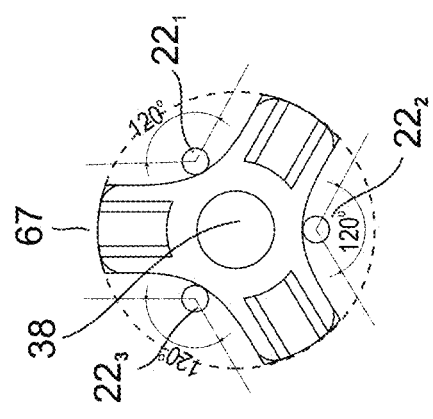

FIG. 9e illustrates a single unit 67 of unitary steerable portion 14 which is designed to allow deflection and yet also stabilizes steerable portion 14 when one or more control wires $22_{1,2,3}$ are pulled.

Each control wire $22_{1,2,3}$, of this configuration of steerable portion 14 (three control wires 22 shown, $22_1$, $22_2$, $22_3$)

controls deflection over an arc of 120 degrees. Such a configuration and control wires 22 positioning stabilizes steerable portion 14 when all three control wires (22$_1$, 22$_2$, 22$_3$) are pulled.

FIG. 9f illustrates a unitary steerable portion 14 constructed from several contiguous units 67 such as those shown in FIG. 9e. Connector 68 functions as a leaf spring-like flexure bar (virtual joint). The extent of Bending of connector 68 is limited by the geometry of the unit (69 at FIG. 9g). Thus deflection of one unit with respect to another will be equal to:

$$\varepsilon = \frac{2}{3} \cdot \frac{l^2 \cdot \sigma}{H \cdot E}$$

Wherein H is the thickness of connector 68, and l is its height. By increasing l and decreasing H each pair of adjacent units become more flexible and less rigid. In such a configuration, the length (L) of steerable portion 14 is determined by the bend radius desired and can be represented by the following: 2πR/4≅L.

Figure 9H:
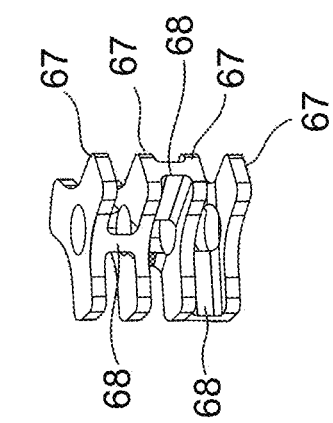

FIG. 9h illustrates a configuration wherein connectors 68 are offset from each other along a series of 4 units 67 to enable defection in various directions. FIG. 9i illustrates a configuration of steerable portion 14 that includes 10 contiguous units 67 with offset connectors 68 and a total length of about 11 mm; force 700 is applied to the distal end of such a unified steerable body 14 (simulating wire 22 pull) to illustrate deflection. When such a force is released, connectors 68 elastically return steerable portion 14 to a linear (normal) configuration.

In the configuration shown in FIGS. 9e-9i, connectors 68 having an l of 0.5 mm, an H of 0.9 mm and a unit 67 with a diameter of 5 mm, will enable a steerable portion 14 11 mm in length to deflect 90 degrees under a pulling force of about 10 N.

Figure 9J:
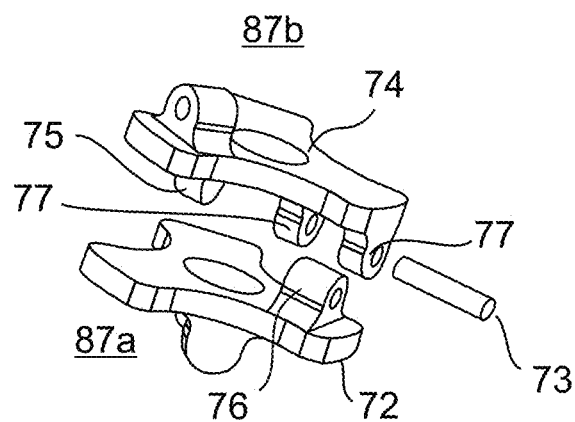
FIGS. 9j-9k illustrate a unitary flexible shaft (FIG. 9k) constructed from disc-like links (FIG. 9j) that are pinned together around a single rotatably-offset pivot point.
Figure 9K:
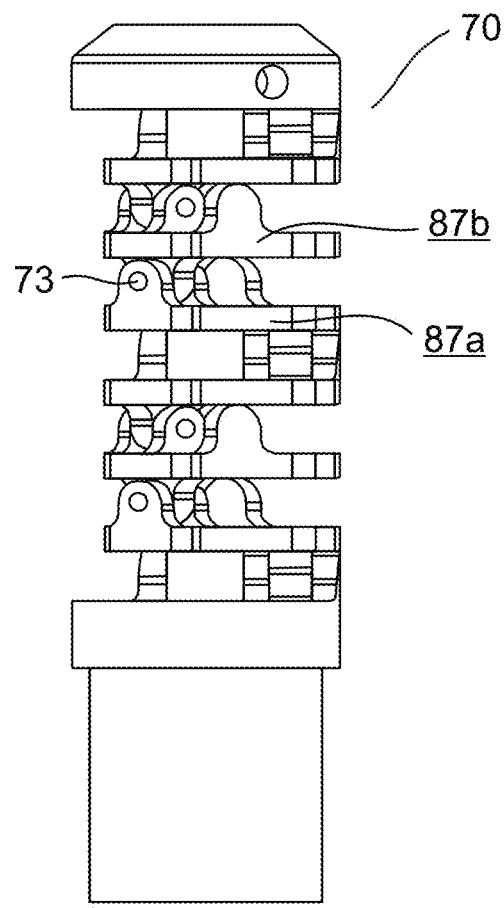

FIGS. 9j-9k illustrate another embodiment of a steerable portion 14 constructed from identical units 67. Each unit 67 has a top face and a bottom face each designed for mating with an opposite face of adjacent unit 67 (i.e. top to bottom and vice versa). As is shown in FIG. 9j, the bottom face of unit 67 includes two engaging elements 77 that connects with unit 67 a with single engaging element 76 of unit 67 that fits into a space between elements 77 of unit 67. When mated, a pin 73 connects elements 77 of unit 67 and element 76 of unit 67 and creates a hinge for allowing articulation. Element 75 acts as a hinge support against compression forces that may act on steerable portion 14. Any number of units 67 can be pinned together in various orientations (rotational offset of hinge region) to create articulation in one of more directions.

Table 1 below exemplifies two unitary articulating regions constructed according to the teachings of the present invention.

TABLE 1

| | Length | Material | Diameter | Bending Radius | Rh | Rt | Pt | Nr |
|---|---|---|---|---|---|---|---|---|
| A | 14 mm | Polyamide (pa 12) | 5 mm | 5 mm | 0.4 mm | 0.3 mm | 1.0 mm | 10 |

TABLE 1-continued

| | Length | Material | Diameter | Bending Radius | Rh | Rt | Pt | Nr |
|---|---|---|---|---|---|---|---|---|
| B | 12 mm | same | 8 mm | 8 mm | 0.5 mm | 0.5 mm | 0.7 mm | 10 |

Figure 12:
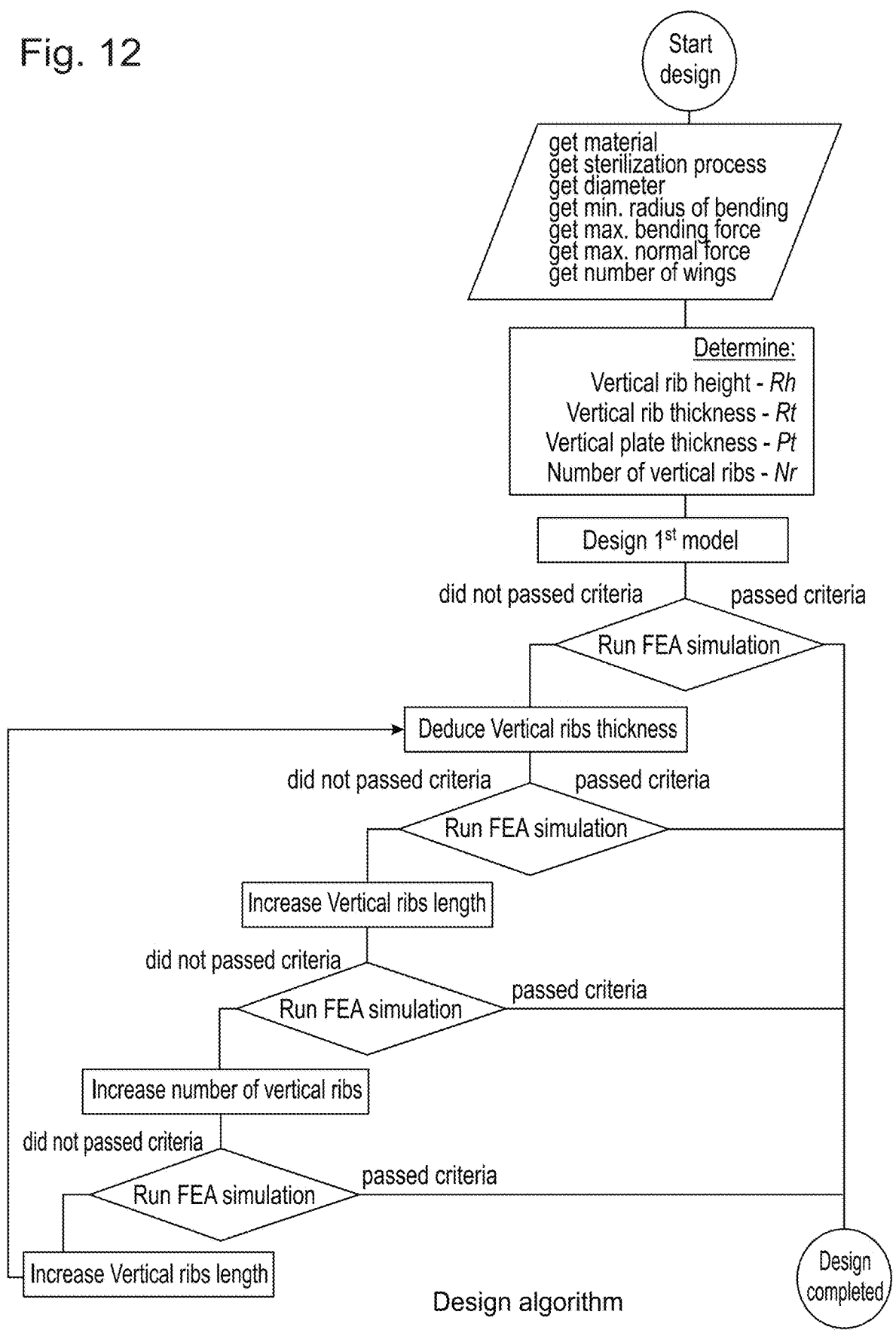
FIG. 12 is a flowchart diagram describing a design 'algorithm' for constructing an articulating region of predetermined properties using the teachings of the present invention.

Rh—vertical height of segment
Rt—vertical thickness of segment 'body'
Pt—vertical height of articulating unit (two segments spaced by 'hinge')
Nr—number of units FIG. 12 describes an 'algorithm' for selecting material properties and unit dimensions based on size and properties of the articulating region.

Device 10 of the present invention can be used in any minimally invasive procedure as follows. An access site is created in a tissue wall and the shaft of device 10 is inserted through the access site and positioned therein using interface 18. If a trocar is used at the access site, device 10 is inserted in a straight configuration. When the effector end of the device is positioned at a target tissue (as ascertained via imaging), the surgeon operates the device through interface 18 as described hereinabove. Following completion of the procedure, the surgeon withdraws the device from the body and the access site is closed.

Steerable portion 14 (constructed from links or as a unitary body) of the entire shaft of device 10 can also be fabricated from a transparent material. Use of a transparent material enables visual inspection of control wires, optical fibers and the like threaded through the device body.

Figure 11B:
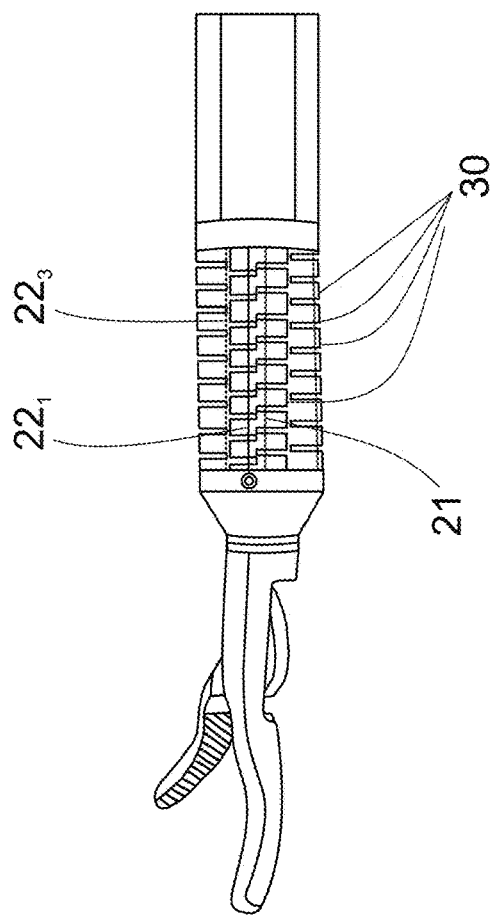
FIGS. 11a-11b illustrate a steerable portion composed of transparent links.
Figure 11A:
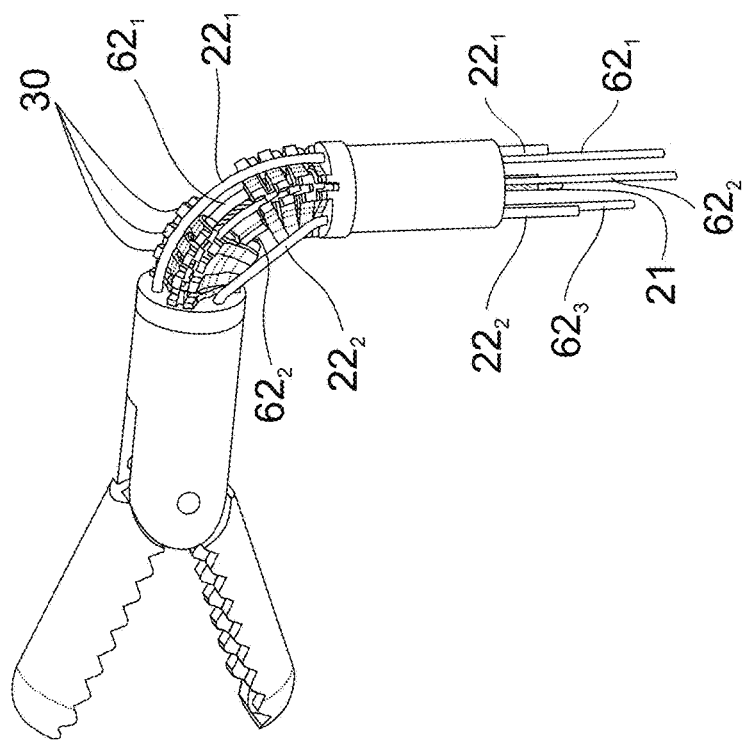

FIG. 11a illustrates a steerable portion 14 constructed from transparent links (some of the links were removed for the sake of clarity). Optic fibers 62$_{1,2,3}$ thread through the shaft from the handle to steerable portion 14, through holes 39 of links 30. FIG. 11b is an image of a prototype constructed with transparent links. The transparent steerable portion enables an operator to see control wires 22$_{2,3}$ and push pull cable 21 through the transparent bodies of links 30.

An illumination source may be connected to the proximal side of optic fibers 62$_{1,2,3}$ at the handle. When illumination is switched on, the transparent articulation radiates light out of steerable portion 14. The light can be visualized by an operator or an assistant, or may serve as a switch for displaying to the operator data such as CT or MRI data of the patient of tissues near the tip of the tool. The light may also serve to track the position of the tool or steerable portion 14 thereof.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non limiting fashion.

Force Measurements in Prototype Device

A test was conducted in order to determine the force needed to deflect a steerable portion of a prototype device by 45° and 90° and to measure the travel length of the wires needed to reach 45° and 90°. Two prototype devices were constructed. The articulation used to test the forces was as describe in details in FIGS. 5a-5d. Two types of steerable portions were tested, one constructed from 5 mm diameter links and another from 8 mm and 5 mm diameter links. Each steerable portion included 9 links manufactured by a rapid prototype printer.

Methods

The shaft of the prototype device was fixed to a table and positioned such that one of the control wires resided on the top side of the shaft. A force measurement device (Shimpo FGN-5b) was attached to this control wire and was fixed to a linear rail. In order to measure forces, the force measurement device was driven away from the shaft until the desired angle of the articulation was measured. The force was recorded and the travel of device was measured.

Results

FIG. 13 summarizes the test results of two prototypes and a prior art Cambridge articulation unit.

As is shown by the results presented in FIG. 13, the forces needed to deflect the steerable portion of the present invention were 10% and 15% (present device 5 or 8 mm respectively) of the forces needed to deflect a commercial tool (Cambridge Endo).

Thus, the present device design requires significantly less (6-10 folds less) force by the operator to deflect the steerable portion. This will enable a surgeon to perform surgery using a manual handle without having to apply large forces, thus substantially improving operability and decreasing device-related fatigue. In addition, when used with an electro-mechanical handle, the present device would not require bulky motors and batteries but would rather be fully operable using small motors and battery packs which would considerably lighten the device and enhance maneuverability thereof.

Another advantage of the present device is shown in FIGS. 10*a*-10*c* which demonstrate the range of articulation and angles of deflection possible with the present device. The present device is capable of 2D and 3D articulation and deflection greater than 180 degrees due to the configuration of the links and in particular the unique routing of cable therein and/or on.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A medical device comprising:
    (a) an elongated device body having a unitary steerable portion including a plurality of contiguous segments, wherein each pair of said contiguous segments is interconnected via a single flexible connector and further wherein flexible connectors of adjacent pairs of said contiguous segments are circumferentially offset by 120 degrees thereby enabling said unitary steerable portion to elastically bend in a plurality of directions away from a longitudinal axis of said elongated device body; and
    (b) three control wires each for controlling deflection over an arc of 120 degrees of a circumference of said elongated device body, said three control wires being unrestrained at said unitary steerable portion such that tensioning of each of said three control wires bends said unitary steerable portion in a different direction and deflects each of said three control wires away from a surface of said unitary steerable portion such that a control wire of said three control wires deflected away from said surface of said unitary steerable portion does not contact said unitary steerable portion.

2. The medical device of claim 1, wherein a bending radius of said unitary steerable portion is 5-8 mm.

3. The medical device of claim 1, further comprising an end effector attached to a distal end of said elongated device body.

4. The medical device of claim 3, wherein said end effector is a grasper, a tissue cutter, or a needle holder.

5. The medical device of claim 1, further comprising a rigid sheath covering non-steerable portions of said elongated device body.

6. The medical device of claim 5, wherein said rigid sheath covers said plurality of control wires at said non-steerable portions.

7. The medical device of claim 1, wherein each of said contiguous segments includes a central disk having a plurality of radially projecting arms.

8. The medical device of claim 7, wherein a control wire of said three control wires resides between two radially projecting arms when said unitary steerable portion is straight.

* * * * *